United States Patent [19]

Rosenblum et al.

[11] Patent Number: 5,767,115
[45] Date of Patent: Jun. 16, 1998

[54] HYDROXY-SUBSTITUTED AZETIDINONE COMPOUNDS USEFUL AS HYPOCHOLESTEROLEMIC AGENTS

[75] Inventors: Stuart B. Rosenblum, West Orange; Sundeep Dugar, Bridgewater; Duane A. Burnett, Fanwood; John W. Clader, Cranford; Brian A. McKittrick, Bloomfield, all of N.J.

[73] Assignee: Schering-Plough Corporation, Kenilworth, N.J.

[21] Appl. No.: 617,751

[22] Filed: Mar. 18, 1996

Related U.S. Application Data

[63] Continuation-in-part of PCT/US94/10099, Sep. 14, 1994, continuation-in-part of Ser. No. 257,593, Jun. 9, 1994, Pat. No. 5,631,365, which is a continuation-in-part of Ser. No. 102,440, Sep. 21, 1993, abandoned.

[51] Int. Cl.$^6$ .................. C07D 205/08; A61K 31/395
[52] U.S. Cl. .......................... 514/210; 540/200
[58] Field of Search .................. 540/200; 514/210

[56] References Cited

U.S. PATENT DOCUMENTS

| | | | |
|---|---|---|---|
| 4,375,475 | 3/1983 | Willard et al. | 424/279 |
| 4,983,597 | 1/1991 | Yang et al. | 514/216 |
| 5,099,034 | 3/1992 | Yoshida | 562/579 |
| 5,350,868 | 9/1994 | Yoshida | 562/579 |

FOREIGN PATENT DOCUMENTS

| | | |
|---|---|---|
| 199630 | 10/1986 | European Pat. Off. |
| 264231 | 4/1988 | European Pat. Off. |
| 337549 | 10/1989 | European Pat. Off. |
| 93/02048 | 2/1993 | WIPO |
| WO94/17038 | 8/1994 | WIPO |

OTHER PUBLICATIONS

Ram et al, *Indian J. Chem.*, Sect B, 29B, 12 (1990), pp. 1134-1137.
Hoekman et al, *J. Agric. Food Chem.*, 30 (1982), pp. 920-924.
Durst et al, *Can. J. Chem.*, 50 (1972), pp. 3196-3201.
Otto et al, *Liebigs Ann. Chem.*, (1983), pp. 1152-1161.
Panfil, et al, *Heterocycles*, 24, 6 (1986), pp. 1609-1617.
Schnitzer-Polokoff, et al, *Comp. Biochem. Physiol.*, 99A (1991), pp. 665-670.
Witzum, *Circulation*, 80, 5 (1989), pp. 1101-1114.
Illingworth, *Drugs*, 36(Supp. 3) (1988), pp. 63-71.
Allain, et al, *Clin. Chem.*, 20, (1974), pp. 470-475.
Horie, et al, *Atherosclerosis*, 88 (1991), pp. 183-192.
Baxter, er al, *J. Biological Chem.*, 267, 17 (1992), pp. 11705-11708.
*Current Drugs: Anti-Atherosclerotic Agents*–Summary Factfile, May, 1992.

Georg et al, *Tet. Letters*, 26, 33 (1985), pp. 3903-3906.
Hart et al, *Tet. Letters*, 45 (1985), pp. 5493-5496.

*Primary Examiner*—Mark L. Berch
*Attorney, Agent, or Firm*—Anita W. Magatti

[57] ABSTRACT

Hydroxy-substituted azetidinone hypocholesterolemic agents of the formula

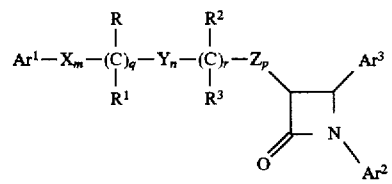

or a pharmaceutically acceptable salt thereof, wherein:

$Ar^1$ and $Ar^2$ are aryl or $R^4$-substituted aryl;

$Ar^3$ is aryl or $R^5$-substituted aryl;

X, Y and Z are —$CH_2$—, —CH(lower alkyl)— or —C(dilower alkyl)—;

R and $R^2$ are —$OR^6$, —$O(CO)R^6$, —$O(CO)OR^9$ or —$O(CO)NR^6R^7$;

$R^1$ and $R^3$ are H or lower alkyl;

q is 0 or 1; r is 0 or 1; m, n and p are 0–4; provided that at least one of q and r is 1, and the sum of m, n, p, q and r is 1–6; and provided that when p is O and r is 1, the sum of m, q and n is 1–5;

$R^4$ is selected from lower alkyl, $R^5$, —$CF_3$, —CN, —$NO_2$ and halogen $R^5$ is selected from —$OR^6$, —$O(CO)R^6$, —$O(CO)OR^9$, —$O(CH_2)_{1-5}OR^6$, —$O(CO)NR^6R^7$, —$NR_6R^7$, —$NR^6(CO)R^7$, —$NR^6(CO)OR^9$, —$NR^6(CO)NR^7R^8$, —$NR^6SO_2R^9$, —$COOR^6$, —$CONR^6R^7$, —$COR^6$, —$SO_2NR^6R^7$, $S(O)_{0-2}R^9$, —$O(CH_2)_{1-10}$—$COOR^6$, —$O(CH_2)_{1-10}CONR^6R^7$, —(lower alkylene)$COOR^6$ and —CH=CH—$COOR^6$;

$R^6$, $R^7$ and $R^8$ are H, lower alkyl, aryl or aryl-substituted Ic $R^9$ is lower alkyl, aryl or aryl-substituted lower alkyl;

are disclosed, as well as a method of lowering serum cholesterol by administering said compounds, alone or in combination with a cholesterol biosynthesis inhibitor, pharmaceutical compositions containing them; and a process for preparing them.

9 Claims, No Drawings

HYDROXY-SUBSTITUTED AZETIDINONE COMPOUNDS USEFUL AS HYPOCHOLESTEROLEMIC AGENTS

The present application is the United States national application corresponding to International Application No. PCT/US94/10099, filed Sep. 14, 1994 and designating the United States, which PCT application is in turn a continuation-in-part of U.S. application Ser. No. 08/257593, filed Jun. 9, 1994, U.S. Pat. No. 5,631,365, which is a continuation-in-part of U.S. application Ser. No. 08/102, 440, filed Sep. 21, 1993, abandoned.

BACKGROUND OF THE INVENTION

The present invention relates to hydroxy-substituted azetidinones useful as hypocholesterolemic agents in the treatment prevention of atherosclerosis, and to the combination of a hydroxy-substituted azetidinone of this invention and a cholesterol bioxynthesis inhibitor for the treatment and prevention of atherosclerosis. The invention also relates to a process for preparing hydroxy-substituteid azetidinones.

Atherosclerotic coronary heart disease (CHD) represents the major cause for death and cardiovascular morbidity in the western world. Risk factors for atherosclerotic coronary heart disease include hypertension, diabetes mellitus, family history, male gender, cigar smoke and serum cholesterol. A total cholesterol level in excess of 225–250 mg/dl is associated with significant elevation of risk of CHD.

Cholesteryl esters are a major component of atherosclerotic lesions and the major storage form of cholesterol in arterial wall cells. Formation of cholesteryl esters is also a key step in the intestinal absorption of dietary cholesterol. Thus, inhibition of cholesteryl ester formation and reduction of serum cholesterol is likely to inhibit the progression of atherosclerotic lesion formation, decrease the accumulation of cholesteryl esters in the arterial wall, and block the intestinal absorption of dietary cholesterol.

A few azetidinones have been reported as being useful lowering cholesterol and/or in inhibiting the formation of cholesterol-containing lesions in mammalian arterial walls. U.S. Pat. No. 4,983,597 discloses N-sulfonyl-2-azetidinones as anticholesterolemic agents and Ram. et al., in *Indian J. Chem.*, Sect. B. 29B, 12 (1990), p. 1134–7, disclose ethyl 4-(2-oxoazetidin-4-yl)phenoxy-alkanoates as hypolipidemic agents. European Patent Publication 264,231 discloses 1-substituted-4-phenyl-3-(2-oxo-alkylidene)-2-azetidinones as blood platelet aggregation inhibitors. European Patent 199,630 and European Patent Application 337,549 disclose elastase inhibitory substituted azetidinones said to be useful treating inflammatory conditions resulting in tissue destruction which are associated with various disease states, e.g. atherosclerosis.

WO93/102048, published Feb. 4, 1993, discloses substituted β-lactams useful as hypocholesterolemic agents.

The regulation of whole-body cholesterol homeostasis in humans and animals involves the regulation of dietary cholesterol and modulation of cholesterol biosynthesis, bile acid biosynthesis and the catabolism of the cholesterol-containing plasma lipoproteinis. The liver is the major organ responsible for cholesterol biosynthesis and catabolism and for this reason, it is a prime determinant of plasma cholesterol levels. The liver is the site of synthesis and secretion of very low density lipoproteins (VLDL) which are subsequently metabolized to low density lipoproteins (LDL) in the circulation. LDL are the predominant cholesterol-carrying lipoproteins in the plasma and an increase in their concentration is correlated with increased atherosclerosis.

When intestinal cholesterol absorption is reduced, by whatever means, less cholesterol is delivered to the liver. The consequence of this action is decreased hepatic lipoprotein (VLDL), production and an increase in the hepatic clearance of plasma cholesterol, mostly as LDL. Thus, the net effect of inhibiting intestinal cholesterol absorption is a decrease in plasma cholesterol levels.

The inhibition of cholesterol biosynthesis by 3-hydroxy-3-methylglutaryl coenzyme A (HMG CoA) reductase (EC1.1.1.34) inhibitors has been shown to be an effective way to reduce plasma cholesterol (Witzum, *Circulation*, 80, 5 (1989), p. 1101–1114) and reduce atherosclerosis. Combination therapy of an HMG CoA reductase inhibitor and a bile acid sequestrant has been demonstrated to be more effective in human hyperlipidemic patients than either agent in monotherapy (Illingworth, Drugs, 36 (Suppl. 3) (1988), p. 63–71).

SUMMARY OF THE INVENTION

Novel hypocholesterolemic compounds of the present invention are represented by the formula I

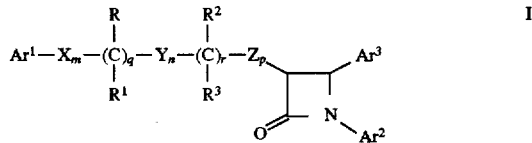

or a pharmaceutically acceptable salt thereof, wherein:

$Ar^1$ and $Ar^2$ are independently selected from the group consisting of aryl and $R^4$-substituted aryl;

$Ar^3$ is aryl or $R^5$-substituted aryl;

X, Y and Z are independently selected from the group consisting of —$CH_2$—, —CH(lower alkyl)— and —C(dilower alkyl)—;

R and $R^2$ are independently selected from the group consisting of —$OR^6$, —O(CO)$R^6$, —O(CO)O$R^9$ and —O(CO)N$R^6R^7$;

$R^1$ and $R^3$ are independently selected from the group consisting of hydrogen, lower alkyl and aryl;

q is 0 or 1; r is 0 or 1; m, n and p are independently 0, 1, 2, 3 or 4; provided that at least one of q and r is 1, and the sum of m, n, p, q and r is 1, 2, 3, 4, 5 or 6; and provided that when p is 0 and r is 1, the sum of m, q and n is 1, 2, 3, 4 or 5;

$R^4$ is 1–5 substituents independently selected from the group consisting of lower alkyl, —$OR^6$, —O(CO)$R_6$, —O(CO)O$R^9$, —O($CH_2$)$_{1-5}$O$R^6$, —O(CO)N$R^6R^7$, —N$R^6R^7$, —$NR^6$(CO)$R^7$, —$NR^6$(CO)O$R^9$, —$NR^6$(CO)N$R^7R^8$, —$NR^6$SO$_2R^9$, —COO$R^6$, —CON$R^6R^7$, —CO$R^6$, —SO$_2$N$R^6R^7$, S(O)$_{0-2}R^9$, —O($CH_2$)$_{1-10}$—COO$R^6$, —O($CH_2$)$_{1-10}$CON$R^6R^7$, —(lower alkylene)COO$R^6$, —CH=CH—COO$R^6$, —$CF_3$, —CN, —$NO_2$ and halogen;

$R^5$ is 1–5 substituents independently selected from the group consisting of —$OR^6$, —O(CO)$R^6$, —O(CO)O$R^9$, —O($CH_2$)$_{1-5}$O$R^6$, —O(CO)N$R^6R^7$, —N$R^6R^7$, —$NR^6$(CO)$R^7$, —$NR^6$(CO)O$R^9$, —$NR^6$(CO)N$R^7R^8$, —$NR^6$SO$_2R^9$, —COO$R^6$, —CON$R^6R^7$, —CO$R^6$, —SO$_2$N$R^6R^7$, S(O)$_{0-2}R^9$, —O($CH_2$)$_{1-10}$—COO$R^6$, —O($CH_2$)$_{1-10}$CON$R^6R^7$, —(lower alkylene)COO$R^6$ and —CH=CH—COO$R^6$;

$R^6$, $R^7$ and $R^8$ are independently selected from the group consisting of hydrogen, lower alkyl, aryl and aryl-substituted lower alkyl; and $R^9$ is lower alkyl, aryl or aryl-substituted lower alkyl.

$R^4$ is preferably 1–3 independently selected substituents, and $R^5$ is preferably 1–3 independently selected substituents. Preferred are compounds of formula I wherein $Ar^1$ is phenyl or $R^4$-substituted phenyl, especially (4-$R^4$)- substituted phenyl. $Ar^2$ is preferably phenyl or $R^4$-substituted phenyl, especially (4-$R^4$)-substituted phenyl. $Ar^3$ is preferably $R^5$-substituted phenyl, especially (4-$R^5$)-substituted phenyl. When $Ar^1$ is (4-$R^4$)-substituted phenyl, $R^4$ is preferably a halogen. When $Ar^2$ and $Ar^3$ are $R^4$- and $R^5$-substituted phenyl, respectively, $R^4$ is preferably halogen or —$OR^6$ and $R^5$ is preferably —$OR^6$, wherein $R_6$ is lower alkyl or hydrogen. Especially preferred are compounds wherein each of $Ar^1$ and $Ar^2$ is 4-fluorophenyl and $Ar^3$ is 4-hydroxyphenyl or 4-methoxyphenyl.

X, Y and Z are each preferably —$CH_2$—. $R^1$ and $R^3$ are each preferably hydrogen. R and $R^2$ are preferably —$OR^6$ wherein $R^6$ is hydrogen, or a group readily metabolizable to a hydroxyl (such as —$O(CO)R^6$, —$O(CO)OR^9$ and —$O(CO)NR^6R^7$, defined above).

The sum of m, n, p, q and r is preferably 2, 3 or 4, more preferably 3. Preferred are compounds wherein m, n and r are each zero, q is 1 and p is 2. Also preferred are compounds wherein p, q and n are each zero, r is 1 and m is 2 or 3. More preferred are compounds wherein m, n and r are each zero, q is 1, p is 2, Z is —$CH_2$ and R is —$OR^6OR_6$, especially when $R^6$ is hydrogen. Also more preferred are compounds wherein p, q and n are each zero, r is 1, m is 2, X is —$CH_2$— and $R^2$ is —$OR^6$, especially when $R^6$ is hydrogen.

Another group of preferred compounds is that wherein $Ar^1$ is phenyl or $R^4$-substituted phenyl, $Ar^2$ is phenyl or $R^4$-substituted phenyl and $Ar^3$ is $R^5$-substituted phenyl. Also preferred are compounds wherein $Ar^1$ is phenyl or $R^4$-substituted phenyl, $Ar^2$ is phenyl or $R^4$-substituted phenyl, $Ar^3$ is $R^5$-substituted phenyl, and the sum of m, n, p, q and r is 2, 3 or 4, more especially 3. More preferred are compounds wherein $Ar^1$ is phenyl or $R^4$-substituted phenyl, $Ar^2$ is phenyl or $R^4$-substituted phenyl $Ar^3$ is $R^5$-substituted phenyl, and wherein m, n and r are each zero, q is 1 and p is 2, or wherein p, q and n are each zero, r is 1 and m is 2 or 3.

This invention also relates to a method of lowering the serum cholesterol level in a mammal in need of such treatment comprising administering an effective amount of a compound of formula I. That is, the use of a compound of the present invention as an hypocholesterolemic agent is also claimed.

In still another aspect, the present invention relates to a pharmaceutical composition comprising a serum cholesterol-lowering effective amount of a compound of formula I in a pharmaceutically acceptable carrier.

The present invention also relates to a method of reducing plasma cholesterol levels, and to a method of treating or preventing atherosclerosis, comprising administering to a mammal in need of such treatment an effective amount of a combination of a hydroxy-substituted azetidinone cholesterol absorption inhibitor of formula I and a cholesterol biosynthesis inhibitor. That is, the present invention relates to the use of a hydroxy-substituted azetidinone cholesterol absorption inhibitor of formula I for combined use with a cholesterol biosynthesis inhibitor (and, similarly, use of a cholesterol biosynthesis inhibitor for combined use with a hydroxy-substituted azetidinone cholesterol absorption inhibitor of formula I) to treat or prevent atherosclerosis or to reduce plasma cholesterol levels.

In yet another aspect, the invention relates to a pharmaceutical composition comprising an effective amount of a hydroxy-substituted azetidinone cholesterol absorption inhibitor of formula I, a cholesterol biosynthesis inhibitor, and a pharmaceutically acceptable carrier. In a final aspect, the invention relates to a kit comprising in one container an effective amount of a hydroxy-substituted azetidinone cho-lesterol absorption inhibitor of formula I in a pharmaceutically acceptable carrier, and in a separate container, an effective amount of a cholesterol biosynthesis inhibitor in a pharmaceutically acceptable carrier.

In yet another aspect, the invention relates to a process for preparing certain compounds of formula I comprising the steps:

(a) treating with a strong base a lactone of the formula

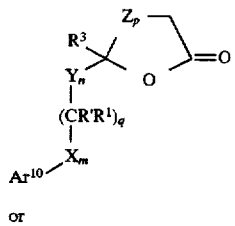

A or

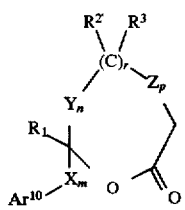

B wherein R' and $R^{2'}$ are R and $R^2$, respectively, or are suitably protected hydroxy groups; $Ar^{10}$ is $Ar^1$, a suitably protected hydroxy substituted aryl or a suitably protected amino-substituted aryl; and the remaining variables are as defined above, provided that in lactone of formula B when n and r are each zero, p is 1–4;

(b) reacting the product of step (a) with an imine of the formula

wherein $Ar^{20}$ is $Ar^2$, a suitably protected hydroxy-substituted aryl or a suitably protected amino-substituted aryl; and $Ar^{30}$ is $Ar^3$, a suitably protected hydroxy-substituted aryl or a suitably protected amino-substituted aryl;

c) quenching the reaction with an acid;

d) optionally removing the protecting groups from R', $R^{2'}$, $Ar^{10}$, $Ar^{20}$ and $Ar^{30}$, when present; and e) optionally functionalizing hydroxy or amino substituents at R, $R^2$, $Ar^1$, $Ar^2$ and $Ar^3$.

Using the lactones shown above, compounds of formula IA and IB are obtained as follows:

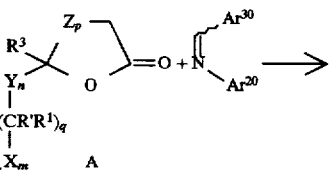

A

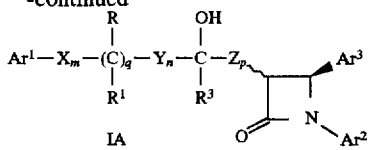

wherein the variables are as defined above; and

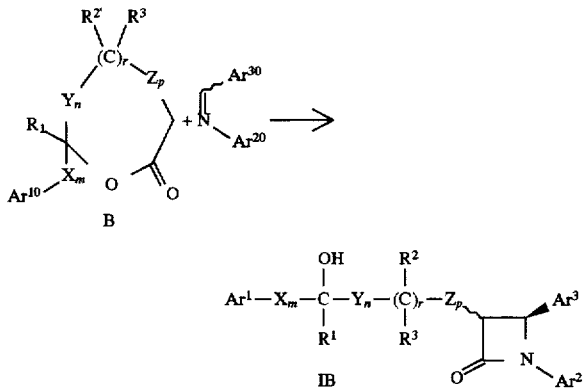

wherein the variables are as defined above.

DETAILED DESCRIPTION

As used herein, the term "lower alkyl" means straight or branched alkyl chains of 1 to 6 carbon atoms.

"Aryl" means phenyl, naphthyl, indenyl, tetrahydronaphthyl or indanyl.

"Halogeno" refers to fluorine, chlorine, bromine or iodine atoms.

The above statement, wherein $R^6$, $R^7$ and $R^8$ are said to be independently selected from a group of substituents, means that $R^6$, $R^7$ and $R^8$ are independently selected, but also that where an $R_6$, $R^7$ or $R^8$ variable occurs more than once in a molecule, those occurrences are independently selected (e.g., if R is —$OR^6$ wherein $R^6$ is hydrogen, $R^4$ can be —$OR^6$ wherein $R^6$ is lower alkyl).

Compounds of the invention have at least one asymmetric carbon atom and therefore all isomers, including enantiomers and diastereomers are contemplated as being part of this invention. The invention includes d and I isomers in both pure form and in admixture including racemic mixtures. Isomers can be prepared using conventional techniques, either by reacting chiral starting materials or by separating isomers of a compound of formula I. Isomers may also include geometric isomers, e.g. when a double bond is present. All such geometric isomers are contemplated for this invention.

Those skilled in the art will appreciate that for some compounds of formula I, one isomer will show greater pharmacological activity than another isomer.

Compounds of the invention with an amino group can form pharmaceutically acceptable salts with organic and inorganic acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salt is prepared by contacting the free base form with a sufficient amount of the desired acid to produce a salt. The free base form may be regenerated by treating the salt with a suitable dilute aqueous base solution such as dilute aqueous sodium bicarbonate. The free base form differs from its respective salt form somewhat in certain physical properties, such as solubility in polar solvents, but the salt is otherwise equivalent to its respective free base form for purposes of the invention.

Certain compounds of the invention are acidic (e.g., those compounds which possess a carboxyl group). These compounds form pharmaceutically acceptable salts with inorganic and organic bases. Examples of such salts are the sodium, potassium, calcium, aluminum, gold and silver salts. Also included are salts formed with pharmaceutically acceptable amines such as ammonia, alkyl amines, hydroxyalkylamines, N-methylglucamine and the like.

Cholesterol biosynthesis inhibitors for use in the combination of the present invention include HMG CoA reductase inhibitors such as lovastatin, pravastatin, fluvastatin, simvastatin, and Cl-981; HMG CoA synthetase inhibitors, for example L-659,699 ((E,E)-11-[3'R-(hydroxy-methyl)-4'-oxo-2'-R-oxetanyl]-3,5,7R-trimethyl-2,4-undecadienoic acid); squalene synthesis inhibitors, for example squalestatin 1; and squalene epoxidase inhibitors, for example, NB-598 ((E)-N-ethyl-N-(6,6-dimethyl-2-hepten-4-ynyl)-3-[(3,3'-bithiophen-5-yl)methoxy]benzene-methanamine hydrochloride) and other cholesterol biosynthesis inhibitors such as DMP-565. Preferred HMG CoA reductase inhibitors are lovastatin, pravastatin and simvastatin.

Compounds of formula I can be prepared by known methods, for example those described below and in WO93/02048.

Method A:

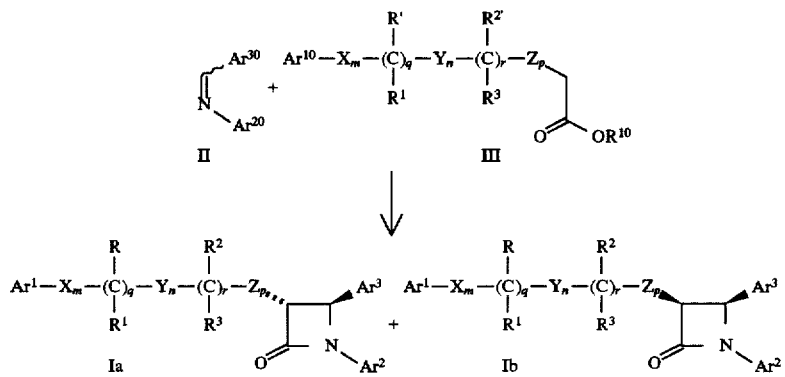

Compounds of formula Ia and Ib, wherein Ar¹, Ar², Ar3, X, Y, Z, R¹, R², R³, m, n, p, q and r are as defined above, can be prepared by treatment of an ester of formula III, wherein R¹⁰ is lower alkyl such as ethyl or a chiral moiety such as menthyl or 10-(diisopropylsulfonamido)isobornyl, and the remaining variables are as defined above, with a strong base such as lithium diisopropylamide (LDA) in a suitable solvent such as tetrrahydrolithium (THF) at −78° C. A solubilizing agent such as hexamethylphosphoric triamide (HMPA) may optionally be added as a cosolvent. An imine of formula 11, wherein Ar²⁰ and Ar³⁰ are as defined above, is added, the reaction mixture is either warmed to room temperature or maintained at a suitable low temperature such as −78° C. for the appropriate time, followed by quenching with a suitable acid such as 1N HCl. The product is isolated using conventional purification techniques. When a protecting group as defined in Table 1 (below) is present on one or more of the optionally protected groups, an additional step comprising removal of the protecting group by conventional techniques is needed. However, for compounds of formula Ia, Ib, or any compound of formula I wherein a protected hydroxy group Ar¹⁰, Ar²⁰, Ar³⁰, R' or R²' is an alkoxy or benzyloxy group, such a protecting group need not be removed to obtain a compound of formula I. When a chiral ester of formula III is used, the resulting compound of formula Ia or Ib is not racemic.

Imines of formula II (Ar³⁰—CH=N—Ar²⁰) can be prepared from aldehydes of the formula Ar³⁰—CHO and amines of the formula Ar⁺—CHO and by procedures well known in the art. Aldehydes of formula Ar⁺—CHO and amines of formula Ar²⁰—NH₂ are commercially available or can be prepared via known procedures.

Method A':

about 5 to about 60 minutes, preferably about 30 minutes. 1–50% of solubilizing cosolvents may optionally be added, preferably about 10% HMPA.

(b) Add an imine of formula 11, wherein Ar²⁰ and Ar³⁰ are as defined above, to the product of step (a) over a period of 5 to 60 minutes, preferably 30 minutes, maintaining the reaction mixture at about 0° C. to about −85° C., preferably about −78° C., for 1 to 12 hours, preferably about 3 hours, or warming the reaction mixture over that time period at a rate of about 10° C. per hour to about 70° C. per hour, preferably about 30° C. per hour, to a temperature of about 20° C.

(c) Quench the reaction with a suitable acid such as HCl (1N).

(d) The protecting groups on R', R²', Ar¹⁰, Ar²⁰ and Ar³⁰, when present, are removed, if desired, by methods well known in the art, for example silyl protecting groups are removed by treatment with fluoride.

e) Compounds of formula I wherein any of R and R², when present, are OR⁶ wherein R⁶ is hydrogen, can be converted by well known methods to other compounds of formula I wherein R and R² are functionalized, i.e., are independently selected from the group consisting of OR⁶ᵃ, —O(CO)R⁶, —O(CO)OR⁹ and —O(CO)NR⁶R⁷, wherein R⁶, R⁷ and R⁹ are as defined above and R⁶ᵃ is lower alkyl, aryl, or aryl-lower alkyl. For example, treatment of the alcohol with an alkyl halide in the presence of a suitable base such as NaH will afford alkoxy-substituted compounds (i.e., R or R² is OR⁶, wherein R⁶ is lower alkyl); treatment of the alcohol with an acylating agent such as acetylchloride will result in compounds wherein R or R² is —OC(O)R⁶; treatment of the alcohol with phosgene followed alcohol of the formula HOR⁹ affords compounds substituted with a —OC

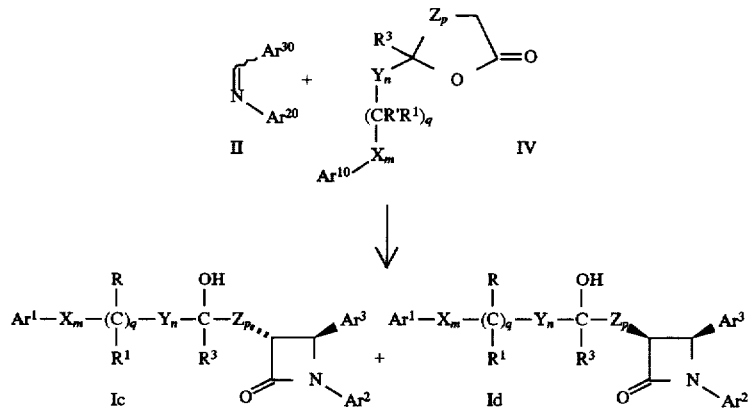

Compounds of formula Ic and Id, wherein the variables are as defined above, can be prepared by a process comprising the following steps:

(a) Treat a lactone of formula IV, wherein the variables are as defined above, with a strong base such as an alkyllithium (e.g., n-butyl-lithium), a metal hydride (e.g., sodium hydride), a metal alkoxide (e.g., sodium methoxide), a metal halide (e.g., TiCl₄), metal exchange of the lithium enolate with a metal halide (e.g., zinc chloride), metal exchange of the lithium enolate with a metal alkyl (e.g., 9-borabicyclononyl triflate), or, preferably, a metalamide (e.g., LDA), in a suitable anhydrous organic solvent such as dry THF, ether or benzene, in a dry, inert atmosphere, e.g., under nitrogen. The reaction is carried out at about 0° C. to about −85° C., preferably about −78° C., over a period of (O)OR⁹ group; and treatment of the alcohol with phosgene followed by an amine of the formula HNR⁶R⁷ affords compounds wherein R or R² is —OC(O)NR⁶R⁷. Compounds of formula I wherein any Ar¹, Ar² or Ar³ has a hydroxy or amino group can be similarly functionalized to obtain other compounds of formula 1, i.e., wherein R⁴ and R⁵ are independently —OR⁶ᵃ, —O(CO)R⁶, —O(CO)OR⁹, —O(CH₂)₁₋₅OR⁶, —O(CO)NR⁶R⁷, —NR⁶R⁷, —NR⁶(CO) R⁷, —NR⁶(CO)OR⁹, —NR⁶(CO)NR⁷R⁸ or —NR⁶SO₂R⁹.

The product of step c, d or e is isolated using conventional purification techniques such as extraction, crystallization or, preferably, silica gel 60 chromatography. When a chiral lactone is used, the resulting compound of formula Ic or Id is not racemic.

Using the procedure described in steps (a)–(e), lactones of formula IVa can be used to prepare compounds of formula Ig and Ih, provided that when n and r are each zero, p is 1–4:

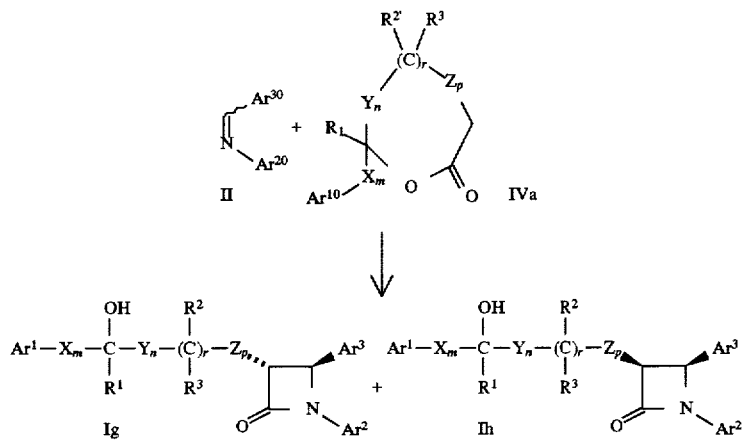

Lactones of formulae IV and IVa are known in the art or can be prepared by methods well known in the art. See, for example, U.S. Pat. No. 4,375,475 and *J. Agric. Food Chem.*, 30 (5) (1982) p. 920–4.

Method B:

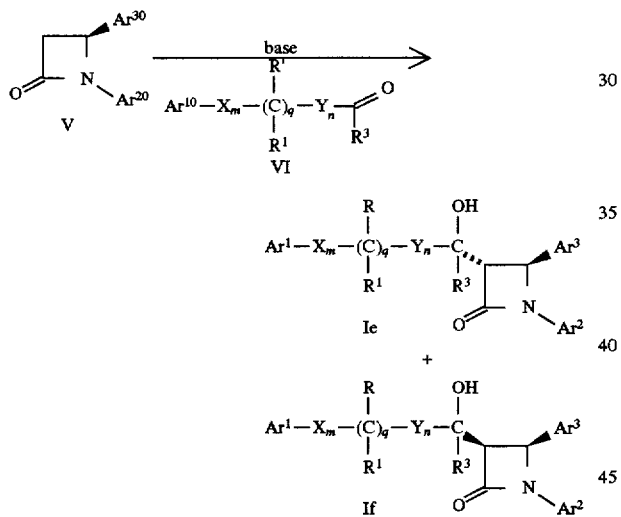

Azetidinones of formula V, wherein $Ar^{20}$ and $Ar^{30}$ are as defined above, can be reacted to form compounds of formula Ie and If i.e., compounds of formula I wherein r is 1, $R^2$ is hydroxy, and p is zero) by treatment of azetidinone V with a strong base such as lithium iosoproptylcyclohexylamide in a suitable solvent such as THF in the presence or absent of HMPA at −78° C., followed by the addition of an aldehyde or ketone of VI, wherein $Ar^{10}$, X, Y, R', $R^1$, $R^3$, m, n and q are as defined above. As in the case of Method A, protecting groups at $Ar^{10}$, $Ar^{20}$, $Ar^{30}$, R' and $R^{2'}$ are removed as necessary.

This process provides several of the possible diastereomers which can be separated by a combination of crystallization, silica gel chromatography and HPLC, using techniques well known in the art. The remaining diastereomers can be obtained by inversion reactions such as the Mitsunobu reaction sequence outlined below, wherein partial structures of formula If are shown:

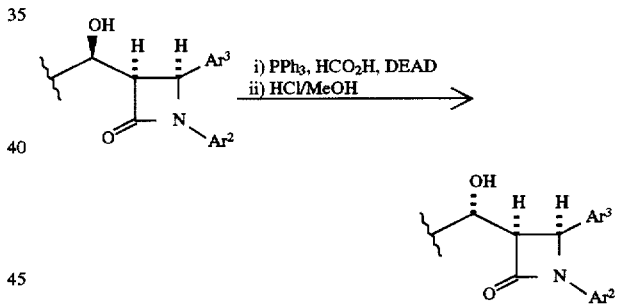

In the above known process, DEAD is diethylazodicarboxylate and $PPh_3$ is triphenylphosphine. The reactants are stirred at room temperature overnight and the resultant formate ester is converted to the corresponding hydroxy compound with the desired stereochemistry.

Method C:

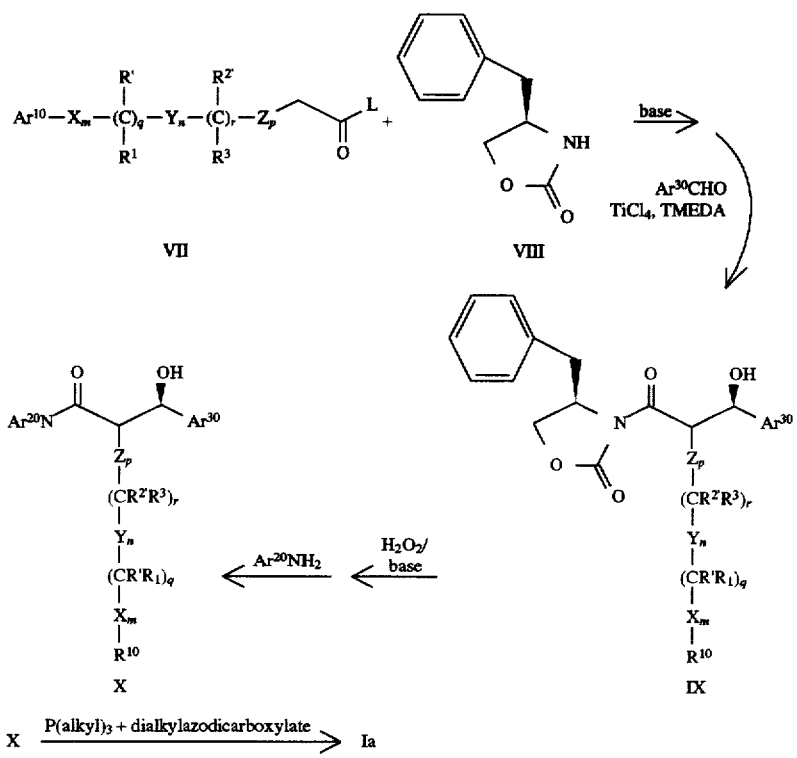

Compounds of formula Ia as defined above can be prepared by reacting a chiral auxiliary such as the compound of formula VIII with an activated carboxylic acid derivative of formula VII, for example an acid chloride (L=Cl), a mixed anhydride formed with phenyl phosphorodichloridate (L=OP(O)(Cl)OPh), an N-methyl-pyridinium ester formed from the reaction of an acid with N-methyl-2-chloropyridinium iodide (L=2-oxy-N-methylpyridinium iodide), and a 2-thiopyridyl ester formed from the reaction of an acid chloride and 2-thiopyridine, wherein the remaining variables are as defined above; enolizing the resultant product, for example with $TiCl_4$ and tetramethylethylenediamine (TMEDA); condensing with an aldehyde, $Ar^{30}CHO$; hydrolyzing to the corresponding acid, then reacting the compound of formula IX with an amine, $Ar^{20}NH_2$; and cyclizing the resultant compound of formula X, with, for example a trialkylphosphine and a dialkylazodicarbo)ylate. As in the case of Method A, protecting groups at $Ar^{10}$, $Ar^{20}$, $Ar^{30}$, R' and $R^{2'}$ are removed as necessary. This procedure is described in detail in WO93/102048.

Method D:

Compounds of formula Ia as defined above can also be prepared treatment of an imine of formula 11, wherein $Ar^{20}$ and $Ar^{30}$ are as defined above, with an activated carboxylic acid derivative of formula VII as defined above in the presence of a tertiary amine base such as triethylamine, tributylamine or diethylisopropylamine in an inert solvent such as $CH_2Cl_2$. Again, as in the case of Method A, protecting groups at $Ar^{10}$, $Ar^{20}$, $Ar^{30}$, R' and $R^{2'}$ are removed as necessary. Use of other bases, e.g., pyridine, favors formation of compounds of formula Ib.

Method E:

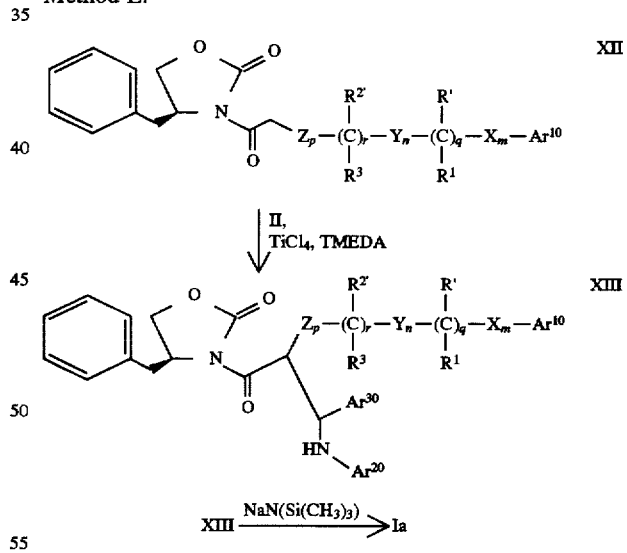

In the first step, compound XII is dissolved in a suitable solvent, e.g., anhydrous $CH_2Cl_2$, and treated with a Lewis acid, e.g., $TiCl_4$ at about −60° C. to 0° C., preferably at about −25° C., under a dry, inert atmosphere, e.g., argon. A tertiary amine base such as TMEDA is added and the mixture stirred at about −60° C. to 0° C., preferably at about −25° C. to −15° C., for a period of about 1 h. An imine of formula $Ar^{30}CH=NAr^{20}$ is added neat or optionally as a solution in a suitable solvent, e.g. anhydrous $CH_2Cl_2$, over a period of about 5 min, and the reaction is stirred vigorously at about −60° C. to 0° C., preferably at about −25° C. to −15° C., for about 3 to 6 h, preferably about 4 h or until the reaction is complete by TLC. An acid, e.g. acetic acid, is added to reaction at the reaction temperature and the mixture is allowed to warm to room temperature slowly with stirring for about 1-3 hours, preferably about 2 hours. The compound of formula XII is isolated by extraction with a suitable solvent, e.g. $CH_2Cl_2$, then purified by crystallization or silica gel chromatography.

In the second step, the product is treated with a strong non-nucleophilic base, such as sodium or lithium bistrimethylsilylamide at about -78° C. to 100° C. After reaction, the mixture is poured into aqueous tartaric acid and the product isolated from the organic layer. As in the case of Method A, protecting groups at $Ar^{10}$, $Ar^{20}$, $Ar^{30}$, R' and $R^{2'}$ are removed as necessary. This process, including the preparation of the starting material of formula XII, is also described in greater detail in WO93/02048.

Method F:

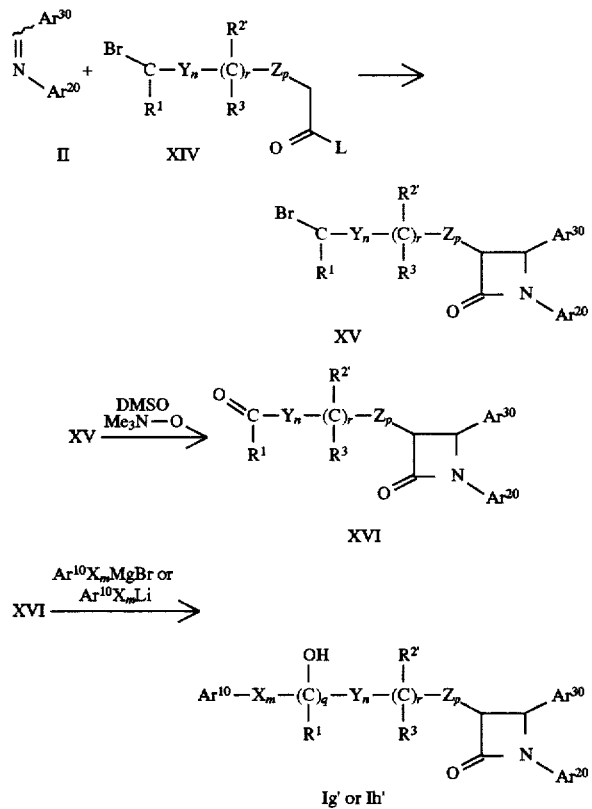

Compounds of formula Ig' and Ih' (i.e., compounds of formula I wherein R is OH), wherein $R^{2'}$ is a protected hydroxy group as defined above, and the remaining variables are as defined above, can be prepared by reacting an imine of formula 11 and a carboxylic acid derivative of formula XIV, wherein the variables are as defined above, according to Method D, followed by oxidation of the resultant halide of formula XV by treatment with an oxidizing agent such as trimethylamine oxide, $CrO_3$ or ozone in a solvent such as DMSO. The resultant aldehyde or ketone of formula XVI is then reacted with an aryl organometallic reagent (e.g., $Ar^{10}X_mMgBr$, $Ar^{10}X_mLi$, $Ar^{10}X_mMgCl$ or $Ar^{10}X_mCeCl_2$) to obtain a compound of formula Ig' or Ih'. As described above, the $Ar^{10}$, $Ar^{20}$, $Ar^{30}$ and $R^{2'}$ substituents can be converted to the desired $Ar^1$, $Ar^2$, $Ar^3$ and $R^2$ substituents by procedures well known in the art.

Method G:

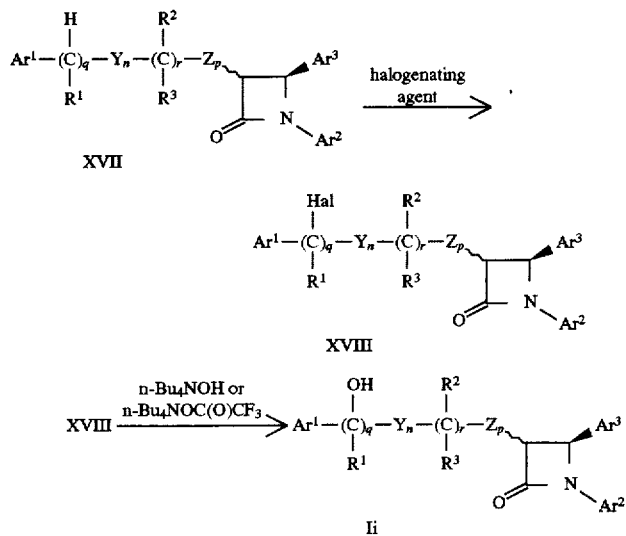

Compounds of formula Ii having a hydroxy substituent on the side chain adjacent to the $Ar^1$ group (i.e., compounds of formula I wherein m is 0) can be prepared by heating a compound of formula XVII, prepared by Method D, above, wherein the variables are as defined above, for about 1-6 hours at about 60° C. to 100° C. with a halogenating agent such as N-bromosuccinimide (NBS) in a suitable solvent such as $CCl_4$ in the presence of an initiating agent such as benzoyl peroxide. The resultant compound of formula XVIII, wherein Hal is Cl, Br or I and the remaining variables are as defined above, is then heated in a suitable solvent such as $CH_2Cl_2$ with a tetraalkyl-ammonium salt such as tetra n-butyl-ammonium hydroxide (n-$Bu_4NOH$) to obtain the compound of formula Ia. Alternatively, compound XVIII can be heated in a suitable solvent such as $CH_2Cl_2$ with tetra n-butylammonium trifluoroacetate (n-$Bu_4NOC(O)CF_3$) followed by treatment with a mild base such as ethanol saturated with NH3 to obtain compound Ii, Method H:

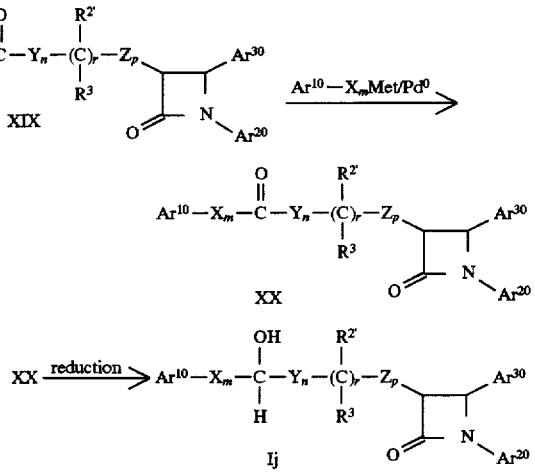

Compounds of formula Ij (i.e., compounds of formula I wherein R is OH, $R^1$ is H and q is 1) are prepared from compound XIX in 2 steps. First, a compound of formula XIX, wherein the variables are as defined above, is dissolved in a suitable anhydrous solvent, e.g. THF, at about -20° C.

to about 22° C., preferably at about 0° C. under a dry inert atmosphere, e.g. argon and adding a transition metal source, e.g. tetrakis(triphenylphosphine)-palladium or palladium acetate/triphenyl phosphine. An organometallic of formula Ar$^{10}$-Xm-Met, wherein in Ar$^{10}$, X and m are as defined above and Met is, for example, ZnCl or B(OH)$_2$, is added to the reaction mixture at about −20° C. to about 22° C., preferably at about 0° C., the reaction mixture is stirred for about 15 min to 4 h, preferably about 1 h, and is then allowed to warm to about 22° C. Addition of dilute acid, e.g. 1N HCl, followed by extraction with a suitable organic solvent, e.g. ethyl acetate (EtOAc), produces compound XX.

The ketone of-formula XX is dissolved in a suitable e.g. CH$_3$OH, a hydrogenation catalyst is added, e.g. Pd on carbon, and the mixture is exposed to H$_2$ gas under a pressure of about 14 psi to 100 psi, preferably about 60 psi for about 1 to 24 h, preferably, about 16 h. The hydrogenation catalyst is removed by filtration and the solvent is removed in vacuo to produce a compound Ij as a mixture of alcohol diastereomers which can be separated by conventional means.

Alternatively, a ketone of formula XX is dissolved in a suitable solvent, e.g. THF, at about −40° C. to about 22° C., preferably at about 0° C., and a suitable reducing agent such as NaBH$_4$, a substituted borohydride (e.g., [cbz-proline]$_3$BHNa) or a borane is adlded, optionally in the presence of a suitable chiral promotor present either in catalytic or stoichiometric amounts, e.g., chiral borane of structures:

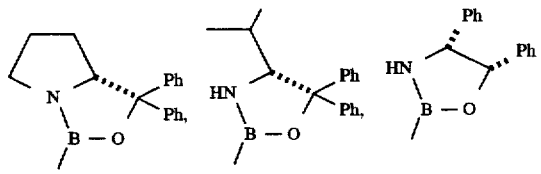

Addition of dilute acid, e.g., 1N HCl, followed by extraction with a suitable solvent produces compounds of formula Ij. As above, protecting groups at Ar$^{10}$, Ar$^{20}$, Ar$^{30}$ and R$^{2'}$ are removed as necessary. When either a chiral reagent or a chiral promotor is used, the resulting product is non-racemic.

Compounds of formula XIX can be prepared by a multi-step procedure as represented below:

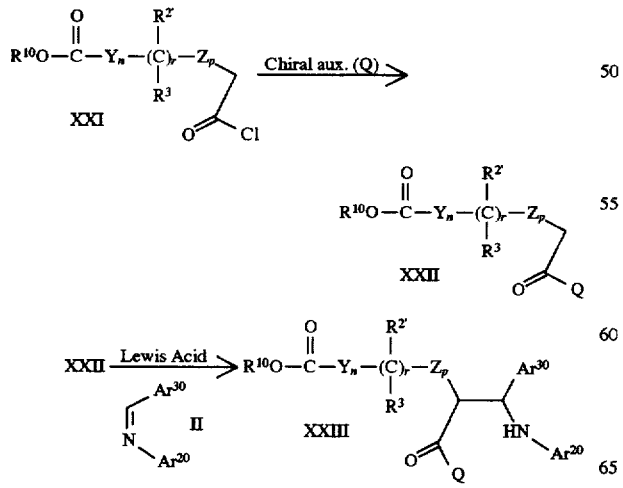

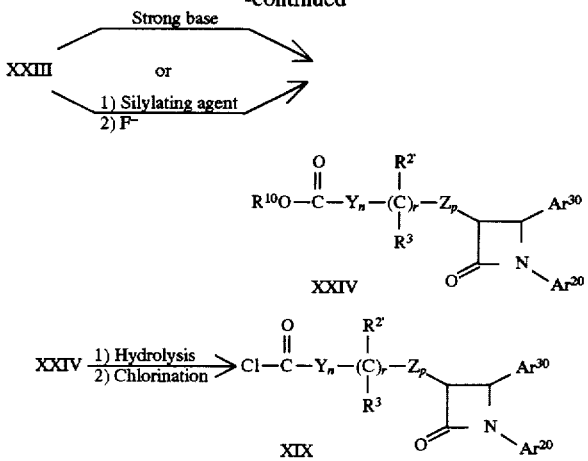

Compounds of formula XXI, wherein R$^{10}$ is lower alkyl and the remaining

Azetidinone ring closure can be accomplished by alternative procedures. By one method, a compound of formula XXIII is treated with a strong non-nucleophilic base, such as sodium or lithium-bistrimethylsilylamide, in a suitable inert organic solvent, e.g. CH$_2$Cl$_2$, at about −78° C. to about 10° C., preferably about 0° C. The mixture is stirred for about 1 to 2 hours while gradually warming to about 22° C. Compound XXIV is isolated by conventional extraction with CH$_2$Cl$_2$. In another, two-step method, a compound of formula XXIII is first treated with mild silylating agent, e.g. N,O-bis(trimethylsilyl)acetamide at about 0° C. to about 100° C., preferably about 40° C. for about 10 min to 60 min, preferably 30 min, then treated with a fluoride anion source, e.g. tetrabutylammonium fluoride (TBAF), at about 0° C. to about 100° C., preferably 40° C., and allowed to stir for about 0.5 to about 4 hours, preferably about 2 hours. Compound XXIV is isolated by conventional extraction methods.

The compound of formula XXIV is hydrolysed by a suitable base, e.g. LiOH, in a suitable solvent, e.g. 66% CH$_3$OH/ water at about 0° C. to about 50° C., preferably 22° C., for about 1 to 4 hours, preferably 2 hours, then extracted with a suitable solvent, e.g. EtOAc. The resulting acid is converted to the acid chloride as described above by treatment with a chlorination agent, e.g. oxalyl chloride, to afford compound Method I:

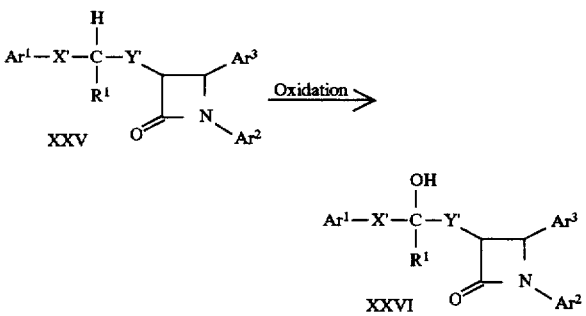

XXVI $\xrightarrow{\text{Reduction}}$ 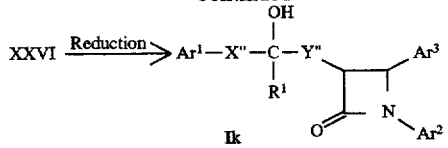
Ik

Compounds of formula Ik, wherein Ar¹, Ar², Ar³ and R¹ are as defined above, one of X" and Y" is —CH₂CH₂— and the other is selected from the group consisting of —CH₂CH₂—, —CH₂—, —CH(lower alkyl)-, —CH (dilower alkyl) and a bond, are prepared by oxidation of an alkene of formula XXV, wherein one of X' and Y' is —CH=CH— and the other is —CH=CH—, —CH₂—, —CH₂CH₂—, —CH(lower alkyl)-, —CH(dilower alkyl) or a bond, and the remaining variables are as defined above, can be prepared by the following two step procedure.

A compound of formula XXV, which can be prepared by Method D, above, is treated with an oxidizing agent such as SeO₂, phenylselenic anhydride or CrO₃ in a suitable solvent such as dioxane at about 22° to 100° C. for about 0.5 to 12 hours. After the starting material is consumed as determined by TLC, or 12 hours, the reaction is cooled to about 22° C. and the product XXVI is isolated by extraction.

In the second step, an allylic alcohol of formula XXVI is dissolved in a suitable solvent, e.g., EtOAc, a hydrogenation catalyst added, e.g., Pd on carbon, and the mixture is exposed to H₂ gas under a pressure of about 14 psi to 60 psi for about 1 to 12 hours. The hydrogenation catalyst is removed in vacuo to obtain a compound of formula Ik.

Method J:

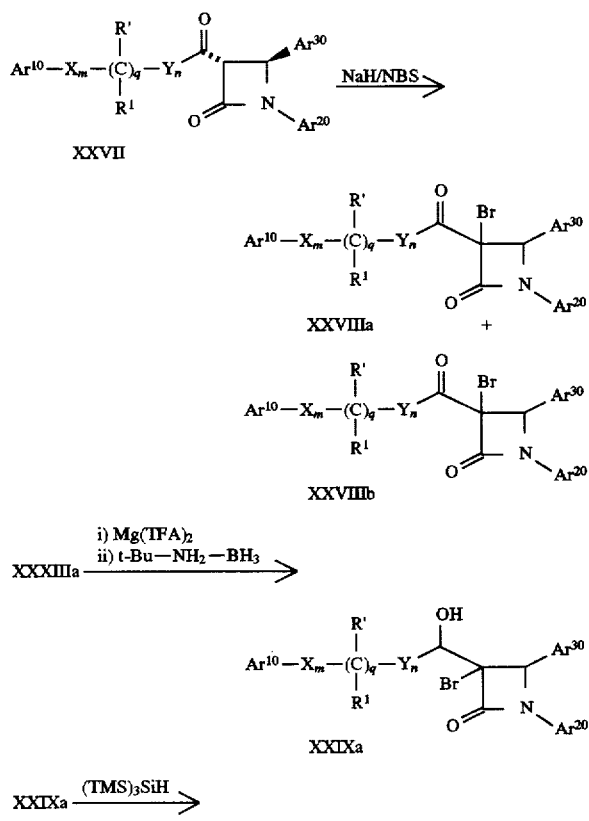

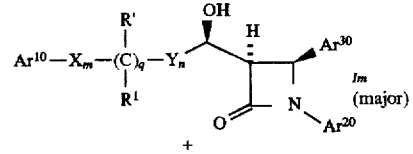

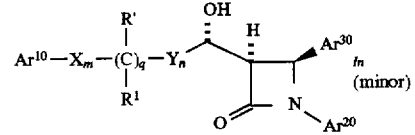

XXVIIIb $\xrightarrow[\text{ii) t-Bu—NH}_2\text{—BH}_3]{\text{i) Mg(TFA)}_2}$

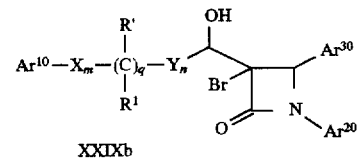

XXIXb $\xrightarrow{(TMS)_3SiH}$ In (major) + Im (minor)

Alcohols of formula Im and In (i.e., compounds of formula I where r is 1, R² is —OH, R³ is hydrogen and p is 0) can be selectively obtained from ketones of formula XXVII in three steps comprising bromination, reduction and debromination. Since the stereochemistry of the major isomers of alcohols XXIXa and XXIXb are different, one can selectively prepare either diastereomeric alcohol.

In the above process, a ketone of formula XXVII, which can be prepared by oxidation of the corresponding hydroxy compound by well known methods, is halogenated, for example by treatment in an inert solvent, e.g., THF, with NaH followed by N-bromosuccinimide, to obtain a mixture of 3-bromo-ketone compounds XXVIII (a and b). Compounds 15 XXVIIIa and XXVIIIb are then separately reduced to the corresponding alcohols, for example by treatment with magnesium trifluoroacetate (Mg(TFA)₂) and t-butylamine borane (t-Bu—NH₂—BH₃) in an inert solvent such as THF at a temperature of about −78° C. to 0° C. The resultant alcohols XXIX are dehalogenated by treatment with tris(trimethylsilyl)silane ((TMS)₃SiH) in a solvent such as toluene in the presence of a radical initiator such as 2,2'-azobisisobutyronitrile (AIBN) to obtain a mixture of isomers Im and In which can be separated into individual enantiomers by conventional means, e.g., HPLC. Again, protecting groups at Ar¹⁰, Ar²⁰, Ar³⁰ and R' are removed as necessary.

Starting compounds III, V, VI, VII, VIII, XIV, XVII, XXI and XXV are all either commercially available or well known in the art and can be prepared via known methods.

Reactive groups not involved in the above processes can be protected during the reactions with conventional protecting groups which can be removed by standard procedures after the reaction. The following Table 1 shows some typical protecting groups:

TABLE 1

| Group to be Protected | Group to be Protected and Protecting Group |
|---|---|
| —COOH | —COOalkyl, —COObenzyl, —COOphenyl |
| \NH/ | \NCOalkyl/, \NCObenzyl/, \NCOphenyl/ |
|  | \NCH$_2$OCH$_2$CH$_2$Si(CH$_3$)$_3$/, \NC(O)OC(CH$_3$)$_3$/ |
|  | \N-benzyl/, \NSi(CH$_3$)$_3$/, \NSi—C(CH$_3$)$_3$/ with CH$_3$ groups |
| —NH$_2$ | —N(succinimide, O=C-CH$_2$-CH$_2$-C=O ring) |
| —OH | —OCH$_3$, —OCH$_2$OCH$_3$, —OSi—C(CH$_3$)$_3$ with CH$_3$ groups |
|  | —OSi(CH$_3$)$_3$, or —OCH$_2$phenyl |

We have found that the compounds of this invention lower serum lipid levels, in particular serum cholesterol levels. Compounds of this invention have been found to inhibit the intestinal absorption of cholesterol and to significantly reduce the formation of liver cholesteryl esters in animal models. Thus, compounds of this invention are hypocholesterolemic agents by virtue of their ability to inhibit the intestinal absorption and/or esterification of cholesterol; they are, therefore, useful in the treatment and prevention of atherosclerosis in mammals, in particular in humans.

The in vivo activity of the compounds of formula I can be determined by the following procedure:

In Vivo Assay of Hypoligidemic Agents Using the Hyperlipidemic Hamster

Hamsters are separated into groups of six and given a controlled cholesterol diet (Purina Chow #5001 containing 0.5% cholesterol) for seven days. Diet consumption is monitored to determine dietary cholesterol exposure in the face of test compounds. The animals are dosed with the test compound once daily beginning with the initiation of diet. Dosing is by oral gavage of 0.2 mL of corn oil alone (control group) or solution (or suspension) of test compound in corn oil. All animals moribund or in poor physical condition are euthanized. After seven days, the animals are anesthetized by intramuscular (IM) injection of ketamine and sacrificed by decapitation. Blood is collected into vacutainer tubes containing EDTA for plasma lipid analysis and the liver excised for tissue lipid analysis. Lipid analysis is conducted as per published procedures (Schnitzer-Polokoff, R., et al, Comp. Biochem. Physiol., 99A, 4 (1991), p. 665–670) and data is reported as percent reduction of lipid versus control.

The present invention also relates to a pharmaceutical composition comprising a compound of formula I and a pharmaceutically acceptable carrier. The compounds of formula I can be administered in any conventional dosage form, preferably an oral dosage form such as a capsule, tablet, powder, cachet, suspension or solution. The formulations and pharmaceutical compositions can be prepared using conventional pharmaceutically acceptable excipients and additives and conventional techniques. Such pharmaceutically acceptable excipients and additives include non-toxic compatible fillers, binders, disintegrants, buffers, preservatives, anti-oxidants, lubricants, flavorings, thickeners, coloring agents, emulsifiers and the like.

The daily hypocholesteremic dose of a compound of formula I is about 0.1 to about 30 mg/kg of body weight per day, preferably about 0.1 to about 15 mg/kg. For an average body weight of 70 kg, the dosage level is therefore from about 5 mg to about 1000 mg of drug per day, given in a single dose or 2–4 divided doses. The exact dose, however, is determined by the attending clinician and is dependent on the potency of the compound administered, the age, weight, condition and response of the patient.

For the combinations of this invention wherein the hydroxy substituted azetidinone is administered in combination with a cholesterol biosynthesis inhibitor, the typical daily dose of the cholesterol biosynthesis inhibitor is 0.1 to 80 mg/kg of mammalian weight per day administered in single or divided dosages, usually once or twice a day: for example, for HMG CoA reductase inhibitors, about 10 to about 40 mg per dose is given 1 to 2 times a day, giving a total daily dose of about 10 to 80 mg per day, and for the other cholesterol biosynthesis inhibitors, about 1 to 1000 mg per dose is given 1 to 2 times a day, giving a total daily dose of about 1 mg to about 200 mg per day. The exact dose of any component of the combination to be administered is determined by the attending clinician and is dependent on the potency of the compound administered, the age, weight, condition and response of the patient.

Where the components of a combination are administered separately, the number of doses of each component given per day may not necessarily be the same, e.g. where one component may have a greater duration of activity, and will therefore need to be administered less frequently.

Since the present invention relates to the reduction of plasma cholesterol levels by treatment with a combination of active ingredients wherein said active ingredients may be administered separately, the invention also relates to combining separate pharmaceutical compositions in kit form. That is, a kit is contemplated wherein two separate units are combined: a cholesterol biosynthesis inhibitor pharmaceutical composition and a hydroxy substituted azetidinone cholesterol absorption inhibitor pharmaceutical composition. The kit will preferably include directions for the administration of the separate components. The kit form is particularly advantageous when the separate components must be administered in different dosage forms (e.g. oral and parenteral) or are administered at different dosage intervals.

Following are examples of preparing compounds of formula I. The stereochemistry listed is relative stereochemistry unless otherwise noted. The terms cis and trans refer to the relative orientations at the azetidinone 3- and 4-positions unless otherwise indicated. The term "J" refers to the proton NMR coupling constant in hertz (Hz) between the 3- and 4-substituted protons of the azetidinone. All NMR data is of CDCl$_3$ solution unless otherwise indicated.

EXAMPLE 1

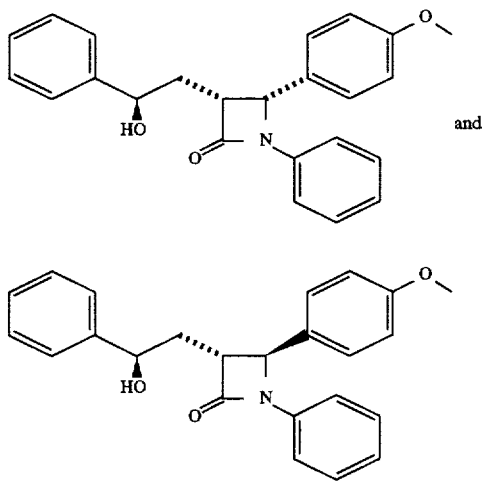

Freshly prepare a solution of lithium diisopropylamide (LDA) by dissolving diisopropylamine (1.19 g, 11.8 mmol) in anhydrous THF (20 ml) at −78° C. under argon. Add n-butyllithium (4.9 ml, 11.8 mmol, 2.4M in hexanes) and stir for 0.5 h at −78° C. To this cold solution add, 4phenylbutyrolactone (1.75 g, 10.8 mmol) in THF (4 ml) over 0.25 h, keeping the reaction temperature below −65° C. Stir at −78° C. for 0.25 h, then add 4-methoxybenzylidine anisidine (2.33 g, 11.0 mmol) in THF (8 ml) over 1 h at −78° C. Warm the reaction slowly to −50° C. over 1 h. Quench the reaction at low temperature with 1N HCl (12 ml). Partition the reaction mixture between ether and 1N HCl, wash the ether layer with water, combine the ether extracts, dry over MgSO$_4$ and concentrate in vacuo. Crystallize the crude reaction residue (3.0 g) from EtOAc-ether to obtain 1.54 g of compound A. Reconcentrate the filtrate and chromatograph on silica gel 60, eluting with 4:1 EtOAc-hexane, and isolate additional compound A (0.385 g) as well as compound B (0.420 g).

Compound A: mp 218°–220° C.; IR 1730 cm-1; CI (M—H) 374; J=5.9 Hz.

Compound B: mp 74°–76° C.; IR 1730 cm-1; CI (M+H) 374; J=2.3 Hz.

Using a similar procedure and appropriate starting materials, prepare compound 1C:

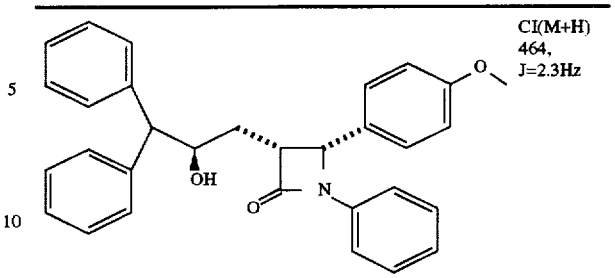

EXAMPLE 2

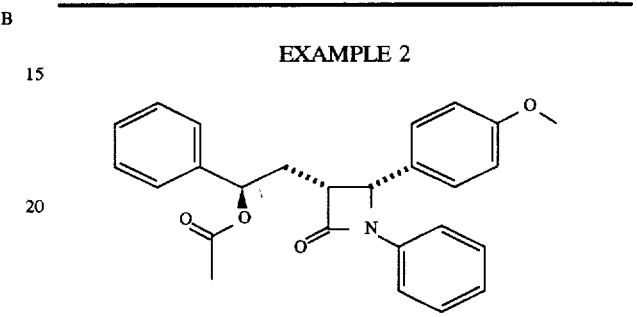

To a solution of compound A from Example 1 (0.5 g, 1.3 mmol) in anhydrous pyridine (2.7 ml), add acetic anhydride (0.63 ml, 6.7 mmol). Stir for 16 h, dilute with CH$_2$Cl$_2$ and wash 3× with 1N HCl 1× with NaCl (sat'd) and 1× with water. Concentrate the organic layer to dryness and crystallize the residue from EtOAc to obtain the title compound (0.46 g), mp 167°–169° C.; IR 1745 cm-1; EI (M+) 415; J=5.9 Hz.

EXAMPLE 3

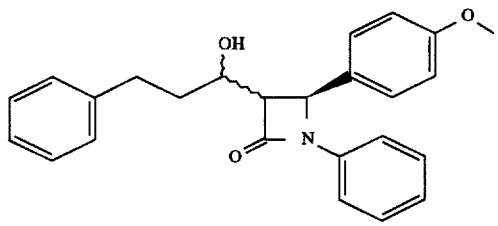

Freshly prepare a solution of lithium isopropylcyclohexylamide (LICA) by adding n-butyllithium (2.84 mL of a 1.6M solution) to 5 a solution of isopropylcyclohexylamine (0.75 mL) in THF (100 mL) at −78° C. Dissolve N-phenyl-4-(4-methoxyphenyl)-2-azetidinone (1.0 g) in THF (8 mL) and slowly add to the LICA solution at −78° C. After stirring for 20 min, add hydrocinnamaldehyde (0.54 g) and stir the reaction mixture at −78° C. for 4 h. Quench the reaction with 10% KHSO$_4$ and extract the product with EtOAc. Separate the organic layer, wash with water and NaCl (sat'd). Concentrate the extract and purify the resultant residue on a silica gel 60 column, eluting with EtOAc:hexane (15:85) to obtain 1.15 g of product as a mixture of diastereomers. Separate the diastereomers by HPLC on a silica gel column to give three diastereomers 3A, 3B and 3C:

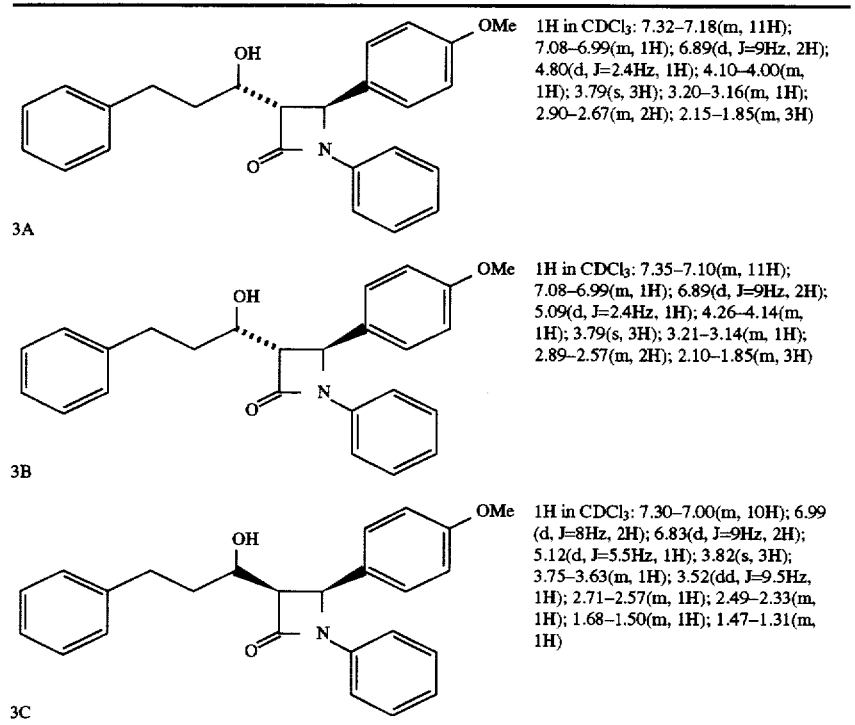
The 3A, 3B and 3C. diastereomers were further separated according to the following reaction scheme, wherein partial structures are shown:
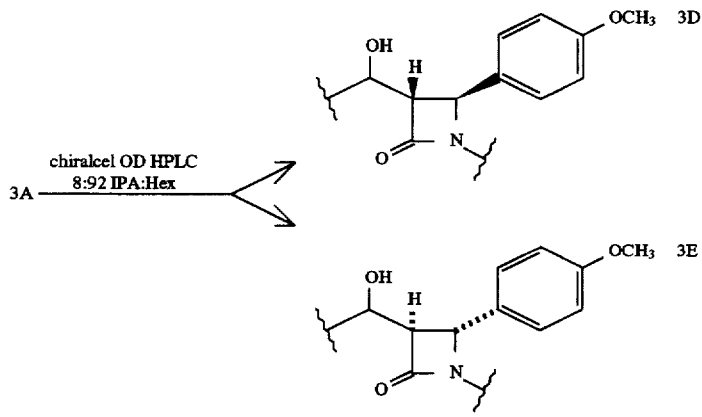

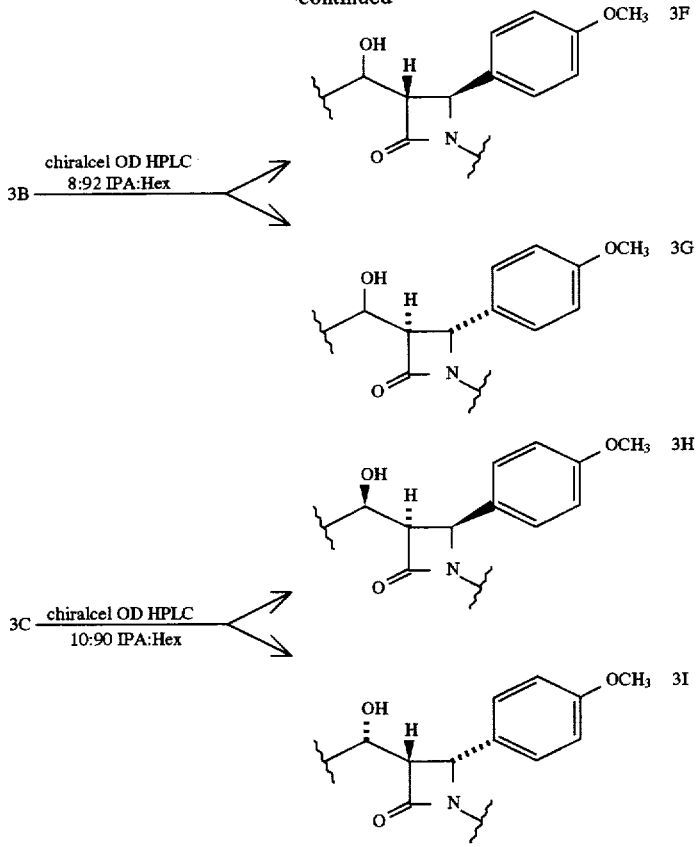

(The following CD spectra data [θ] are all obtained in CH$_3$OH.)

3D) $[\theta]_{227nM}$=+2.0×10$^4$ cm$^2$/dM; $[\theta]_{241nM}$=−4.6×10$^4$ cm$^2$/dM. Elemental analysis calc for C$_{25}$H$_{25}$NO$_3$−0.25 H$_2$O: C 76.6; H 6.56 N 3.57. found: C 76.66; H 6.49; N 3.64.

3E) $[\theta]_{227nM}$=−1.95×10$^4$ cm$^2$/dM; $[\theta]_{241nM}$=+4.45×10$^4$ cm$^2$/dM. Elemental analysis calc for C$_{25}$H$_{25}$NO$_3$.0.5 H$_2$O: C 75.73; H 6.61; N 3.53. found: C 75.66; H 6.41; N 3.60.

3F) $[\theta]_{226nM}$=+1.97×10$^4$ cm$^2$/dM; $[\theta]_{240nM}$=−5.22×10$^4$ cm$^2$/dM. Elemental analysis calc for C$_{25}$H$_{25}$NO$_3$: C 77.48; H 6.5−1; N 3.62. found: C 77.44; H 6.53; N 3.70.

3G) $[\theta]_{226nM}$=−1.78×10$^4$ cm$^2$/dM; $[\theta]_{241nM}$=+4.78×10$^4$ cm$^2$/dM (CIMS 388 M$^+$H).

3H) $[\theta]_{226nM}$=+2.24×10$^4$ cm$^2$/dM; $[\theta]_{241nM}$=−5.4×10$^4$ cm$^2$/dM. $[\alpha]_D^{25}$=−54.4° (2.5 mg/ml CH$_3$OH) Elemental analysis calc for C$_{25}$H$_{25}$NO$_3$: C 77.48; H 6.51; N 3.62. found: C 77.11; H 6.50; N 3.72.

3I) $[\theta]_{226nM}$=−2.05×10$^4$ cm$^2$/dM; $[\theta]_{241nM}$=+5.2×10$^4$ cm$^2$/dM. (CIMS 388 M$^+$H).

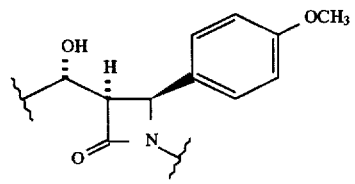

3J)

Add DEAD (0.11 ml) to a solution of compound 3H (132 mg), PPh$_3$ (0.18 g) and HCO$_2$H (39 ml) in THF (5 ml). Stir at room temperatq overnight, then partition the reaction mixture between Et$_2$O and H$_2$O. Wash (brine) and dry (MgSO$_4$) the organic layer and concentrate to dryness. Flash chromatograph the residue using EtOAc:Hex (1:4) to obtain the formate ester. Dissolve this in CH$_3$OH and add 4 drops of conc. HCl. After 4 h, concentrate in vacuo and flash chromatograph the residue using EtOAc:Hex (1:3) to obtain 3J. $[\theta]_{224nM}$=+2.54×10$^3$ cm$^2$/dM;

$[\theta]_{239nM}$=+5.70×10$^4$ cm$^2$/dM. $[\alpha]_D^{20}$=−157.6° (2.5 mg/ml CH$_3$OH)

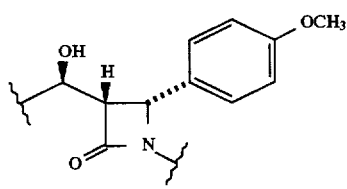

3K)

Using the procedure described for 3J, treat compound 3I to obtain 3K. $[\theta]_{222nM}$=−3.4×10$^3$ cm$^2$/dM; $[\alpha]_{240nM}$=−5.6×10$^4$ cm$^2$/dM. $[\alpha]_D^{20}$=+167.2° (2.5 mg/ml CH$_3$OH)

Using the procedure described above for preparing compounds 3A and 3B, treat N-phenyl-4-(4-methoxyphenyl)-2-azetidinone with LICA followed by 2-naphthaldehyde to obtain the diastereomers 3L and 3M:

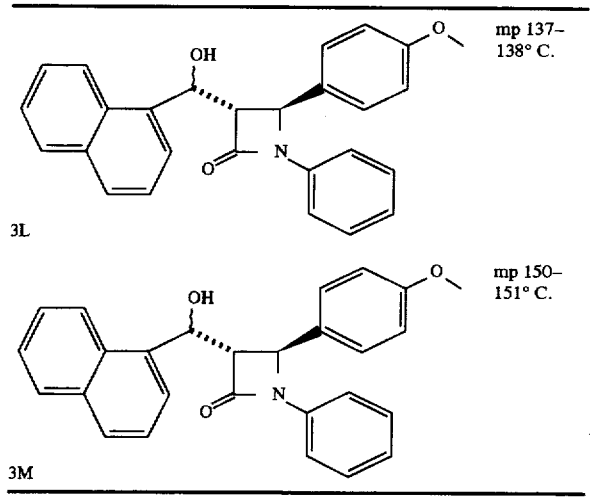

3L    mp 137–138° C.

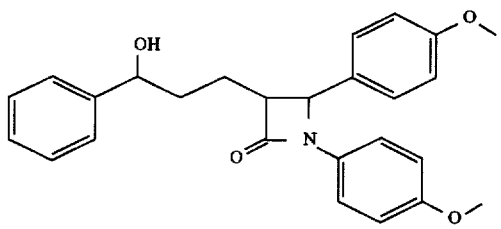

3M    mp 150–151° C.

EXAMPLE 4

Method 1:

Step 1) To a refluxing solution of 4-methoxybenzylidene anisidine (10.0 g, 41.5 mmol) and tributylamine (20.8 ml, 87 mmol) in toluene (100 ml), add 5-bromovaleroyl chloride (8.5 g, 43, mmol) in toluene (20 ml) dropwise over 2 h. Stir the reaction mixture at 80° C. for 12 h, cool to room temperature, wash 3× with 1 N HCl, 1× with water and dry the organic layer over $MgSO_4$. Purify by silica gel chromatography, eluting with ethyl acetate:hexane (4:1) to obtain 5.1 g of (3R, 4S)-1,4-bis(4-methoxyphenyl)-3-(3-bromopropyl)-2-azetidinone (relative stereochemistry), mp 70°–73° C.; EI ($M^+$) 404; J=2.3 Hz.

Step 2) To a solution of the product of step 1 (5.1 g, 12.6 mmol) in $(CH_3)_2SO$ (20 ml), add $(CH_3)_3N(O)$ (2.39 g, 31.9 mmol). Heat the mixture at 60° C. for 3 h, cool to room temperature, dilute with EtOAc, and wash 3× with water. Combine the aqueous fractions and extract with EtOAc. Combine the organic fractions and concentrate. Purify the crude product by silica gel chromatography, eluting with EtOAc:hexane (1:1) to obtain 1.4 g (3R, 4S)-1,4-bis-(4-methoxyphenyl)-2-oxo-3-azetidine-propanol (relative stereochemistry), an oil; EI ($M^+$) 339; J=2.3 Hz.

Step 3) To a solution of the product of step 2 (0.7134 g, 2.2 mmol) in THF (4 ml) at 0° C., add phenylmagnesium bromide (2.4 ml, 2.4 mmol, 1.0 M in THF) over 0.25 h. After 1 h at 0° C., add water (5 ml), separate the layers, wash the organic layer 1 × with 1N HCl, dry with $MgSO_4$ and concentrate to an oil. Purify by silica gel chromatography, eluting with EtOAc:hexane (2:1) to obtain 0.372 g of the title compound (mix of diastereomers) as an oil. CI ($M^+H$) 418.

Separation of diastereomers: Apply the diastereomeric mixture from step 3 to a Chiralcel OD (Chiral Technologies Corp. Pa.) chromatography column, eluting with hexane:ethanol (9:1) to obtain enantiomerically pure (>98%) diastereomers as follows:

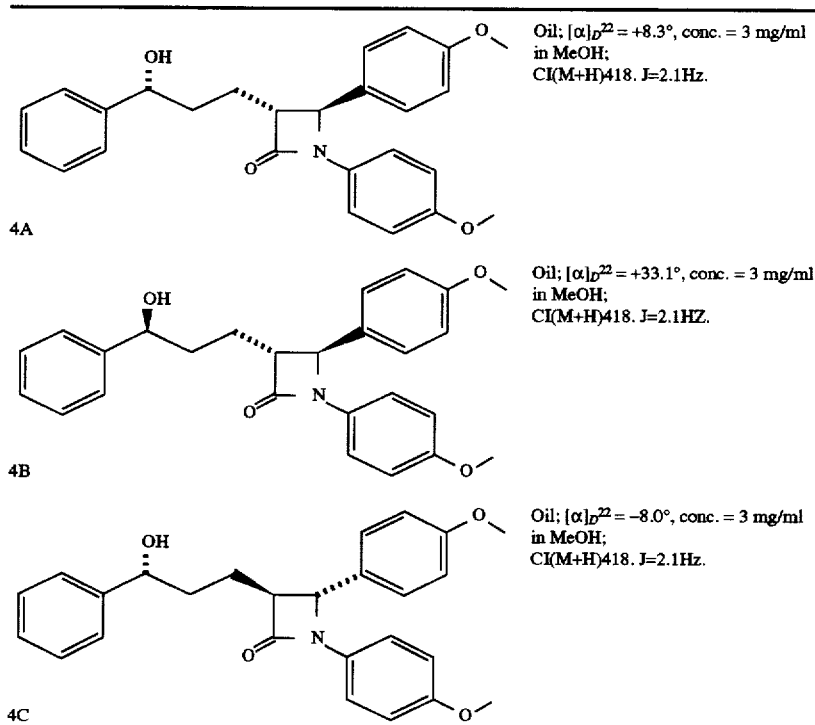

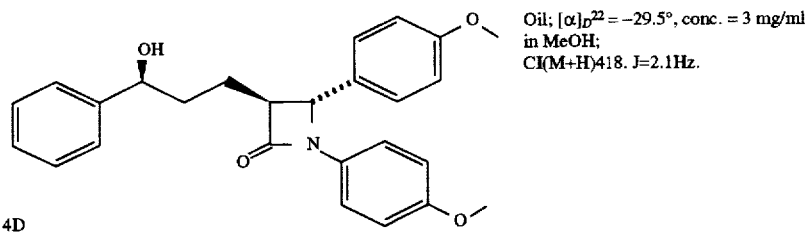

Oil; $[\alpha]_D^{22} = -29.5°$, conc. = 3 mg/ml in MeOH; CI(M+H)418. J=2.1Hz.

4D

Method 2:

Step 1) To a solution of 1,4-(S)-bis(4-methoxyphenyl)-3-(3(R)-phenylpropyl)-2-azetidinone (5.04 g, 0.013 mole) in $CCl_4$ (20 ml) at 80° C., add NBS (2.76 g, 0.0155 mole) and benzoyl peroxide (0.24 g, 1.0 mmole) in three equal portions over 1 h. Follow the reaction by TLC (4:1 hexane: EtOAc). Cool the reaction to 22° C., add $NaHSO_4$, separate the layers and wash the organic layer 3× with water. Concentrate the organic layer to obtain the crude product.

CI ($M^+H$) 480; $^1H$ in $CDCl_3$ δ PhC$\underline{H}$(OH)=5.05 ppm.

Step 2) Dissolve the crude product of Step 1 in $CH_2Cl_2$ (30 ml) and add 40% n-BuNOC(O)$CF_3$ in water (30 ml). Reflux the biphasic reaction for 24 h, cool, separate the layers and wash the organic layer 6× with water. Concentrate the organic layer to dryness and immediately redissolve the residue in ethanol saturated with $NH_3$ (10 ml). After 1 h, concentrate the reaction mixture and partially purify by silica gel chromatography. Further purify by HPLC to obtain a 1:1 mixture of compounds 4A and 4B. The mixture can be further purified on a Chiracel OD column to obtain 4A and 4B separately as characterized above.

Using the procedure described in Example 4, Method 2, with 4(S)-(4-acetoxyphenyl)-3(R)-(3-phenylpropyl)-1-(4-methoxy-phenyl)-2-azetidinone as the starting material, prepare the following compounds:

EXAMPLE 5

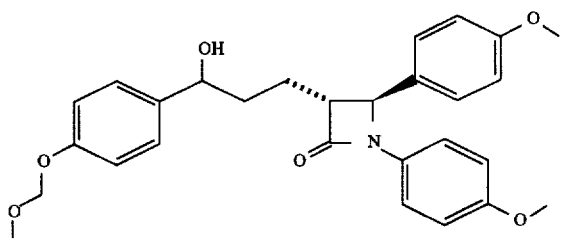

To a solution of the product of step 2 of Example 4 (0.230 g, 0.68 mmol) in THF (2 ml), add the reagent derived from treatment of 4-methoxymethylphenyl bromide (0.159 g, 0.736 mmol) in THF (4 ml) at −78° C. with sec-butyllithium (0.6 ml, 0.78 mol, 1.3M in hexanes), followed by $CeCl_3$ (0.186 g, 0.75 mmol). After 4 h, extract the product and purify by chromatography in a manner similar to that described in step 3 of Example 4 to obtain 0.05 g of the title compound (mix of diastereomers) as an oil. CI ($M^+H$) 478.

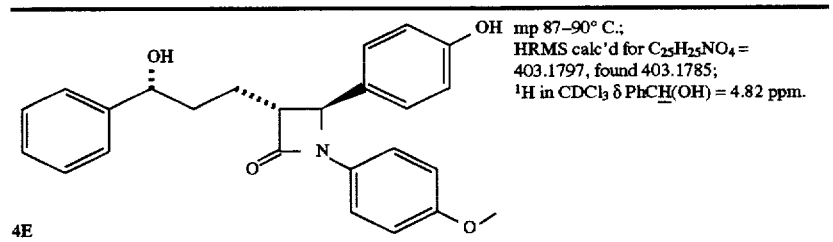

mp 87–90° C.;
HRMS calc'd for $C_{25}H_{25}NO_4$ = 403.1797, found 403.1785;
$^1H$ in $CDCl_3$ δ PhC$\underline{H}$(OH) = 4.82 ppm.

4E

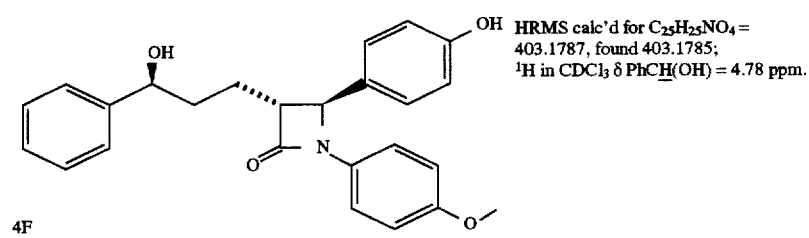

HRMS calc'd for $C_{25}H_{25}NO_4$ = 403.1787, found 403.1785;
$^1H$ in $CDCl_3$ δ PhC$\underline{H}$(OH) = 4.78 ppm.

4F

EXAMPLE 6

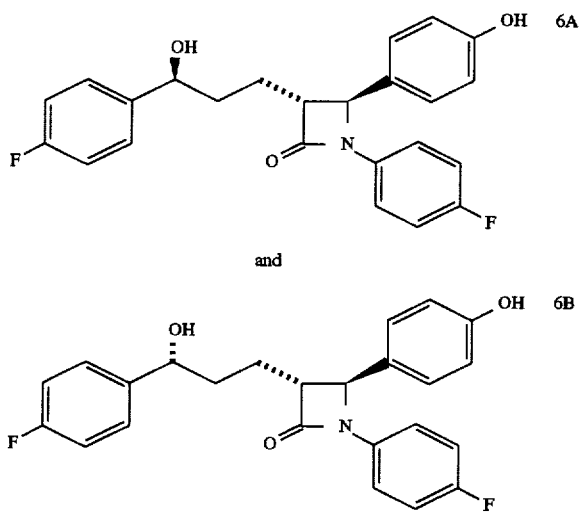

Step 1): To a solution of (S)-4-phenyl-2-oxazolidinone (41 g, 0.25 mol) in CH$_2$Cl$_2$ (20 ml), add 4-dimethylaminopyridine (2.5 g, 0.02 mol) and triethylamine (84.7 ml, 0.61 mol) and cool the reaction to 0° C. Add methyl-4-(chloroformyl)butyrate (50 9, 0.3 mol) as a solution in CH$_2$Cl$_2$ (375 ml) dropwise over 1 h, and allow the reaction to warm to 22° C. After 17 h, add water and H$_2$SO$_4$ (2N, 100 ml), separate the layers, and wash the organic layer sequentially with NaOH (10%), NaCl (sat'd) and water. Dry the organic layer over MgSO$_4$ and concentrate to obtain a semicrystalline product.

Step 2): To a solution of TiCl$_4$ (18.2 ml, 0.165 mol) in CH$_2$Cl$_2$ (600 ml) at 0° C., add titanium isopropoxide (16.5 ml, 0.055 mol). After 15 min, add the product of Step 1 (49.0 9, 0.17 mol) as a solution in CH$_2$Cl$_2$ (100 ml). After 5 min., add diisopropylethylamine (DIPEA) (65.2 ml, 0.37 mol) and stir at 0° C. for 1 h, cool the reaction mixture to –20° C., and add 4-benzyloxybenzylidine(4-fluoro)aniline (114.3 g, 0.37 mol) as a solid. Stir the reaction vigorously for 4 h at –20° C., add acetic acid as a solution in CH$_2$Cl$_2$ dropwise over 15 min, allow the reaction to warnr to 0° C., and add H$_2$SO$_4$ (2N). Stir the reaction an additional 1 h, separate the layers, wash with water, separate and dry the organic layer. Crystallize the crude product from ethanol/water to obtain the pure intermediate.

Step 3): To a solution of the product of Step 2 (8.9 g, 14.9 mmol) in toluene (100 ml) at 50° C., add N,O-bis(trimethylsilyl)acetamide (BSA) (7.50 ml, 30.3 mmol). After 0.5 h, add solid TBAF (0.39 g, 1.5 mmol) and stir the reaction at 50° C. for an additional 3 h. Cool the reaction mixture to 22° C., add CH$_3$OH (10 ml), wash the reaction mixture with HCl (1N), NaHCO$_3$ (1N) and NaCl (sat'd.), and dry the organic layer over MgSO$_4$.

Step 4): To a solution of the product of Step 3 (0.94 g, 2.2 mmol) and CH$_3$OH (3 ml), add water (1 ml) and LiOH.H$_2$O (102 mg, 2.4 mmole). Stir the reaction at 22° C. for 1 h and add additional LiOH.H$_2$O (54 mg, 1.3 mmole). After a total of 2 h, add HCl (1N) and EtOAc, separate the layers, dry the organic layer and concentrate in vacuo. To a solution of resultant product (0.91 g, 2.2 mmol) in CH$_2$Cl$_2$ at 22° C., add ClCOCOCl (0.29 ml, 3.3 mmol) and stir for 16 h. Remove the solvent in vacuo.

Step 5): To an efficiently stirred suspension of 4-fluorophenylzinc chloride (4.4 mmol) prepared from 4-fluorophenylmagnesium bromide 5 (1M in THF, 4.4 ml, 4.4 mmol) and ZnCl$_2$ (0.6 g, 4.4 mmol) at 4° C., add tetrakis(triphenylphosphine)palladium (0.25 g, 0.21 mmol) and the product of Step 4 (0.94 g, 2.2 mmol) as a solution in THF (2 ml). Stir the reaction for 1 h at 0° C. and then for 0.5 h at 22° C. Add HCl (1N, 5 ml) and extract with EtOAc. Concentrate the organic layer to an oil and purify by silica gel chromatography to obtain 1 -(4-fluorophenyl)-4(S)-(4-hydroxyphenyl)-3(R)-(3-oxo-3-phenylpropyl)-2-azetidinone:

HRMS calc'd for C$_{24}$H$_{19}$F$_2$NO$_3$=408.1429, found 408.1411.

Step 6): To the product of Step 5 (0.95 g, 1.91 mmol) in THF (3 ml), add (R)-tetrahydro-1-methyl-3,3-diphenyl-1H, 3H-pyrrolo-[1,2-c][1,3,2]oxazaborole (120 mg, 0.43 mmol) and cool the mixture to –20° C. After 5 min, add borohydride-dimethylsulfide complex (2M in THF:, 0.85 ml, 1.7 mmol) dropwise over 0.5 h. After a total of 1.5 h, add CH$_3$OH followed by HCl (1 N) and extract the reaction mixture with EtOAc to obtain 1-(4-fluorophenyl)-3(R)-[3 (S)-(4-fluorophenyl)-3-hydroxypropyl)]-4(S)-[4-(phenylmethoxy)phenyl]-2-azetidinone (compound 6A-1) as an oil. $^1$H in CDCl$_3$ δ H3=4.68, J=2.3 Hz, CI (M$^+$H) 500.

Use of (S)-tetra-hydro-1 -methyl-3,3-diphenyl-1 H,3H-pyrrolo-[1,2-c][1,3,2] oxazaborole gives the corresponding 3(R)-hydroxypropyl azetidinone (compound 6B-1). $^1$H in CDCl$_3$ δ H3=4.69, J=2.3 Hz, CI (M$^+$H) 500.

To a solution of compound 6A-1 (0.4 g, 0.8 mmol) in ethanol (2 ml), add 10% Pd/C (0.03 g) and stir the reaction under a pressure (60 psi) of H$_2$ gas for 16 h. Filter the reaction mixture and concentrate the solvent to obtain compound 6A. Mp 164°–166° C.; CI (M$^+$H) 410.

$[\alpha]_D^{25}$=–28.1° (c 3, CH$_3$OH). Elemental analysis calc'd for C$_{24}$H$_{21}$F$_2$NO$_3$; C 70.41; H 5.17; N 3.42; found C 70.25; H 5.19; N 3.54.

Similarly treat compound 6B-1 to obtain compound 6B. Mp 129.5°–132.5° C.; CI (M$^+$H) 410. Elemental analysis calc'd for C$_{24}$H$_{21}$F$_2$NO$_3$; C 70.41; H 5.17; N 3.42; found C 70.30; H 5.14; N 3.52.

Step 6') (Alternative): To a solution of the product of Step 5 (0.14 g, 0.3 mmol) in ethanol (2 ml), add 10% Pd/C (0.03 g) and stir the reaction under a pressure (60 psi) of H$_2$ gas for 16 h. Filter the reaction mixture and concentrate the solvent to afford a 1:1 mixture of compounds 6A and 6B.

Using appropriate starting materials and following the procedure of steps 1–6, prepare the following compounds:

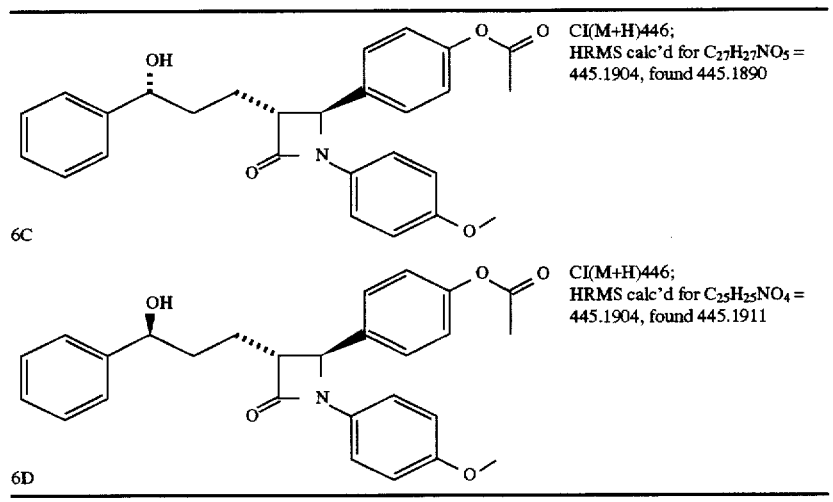

EXAMPLE 7

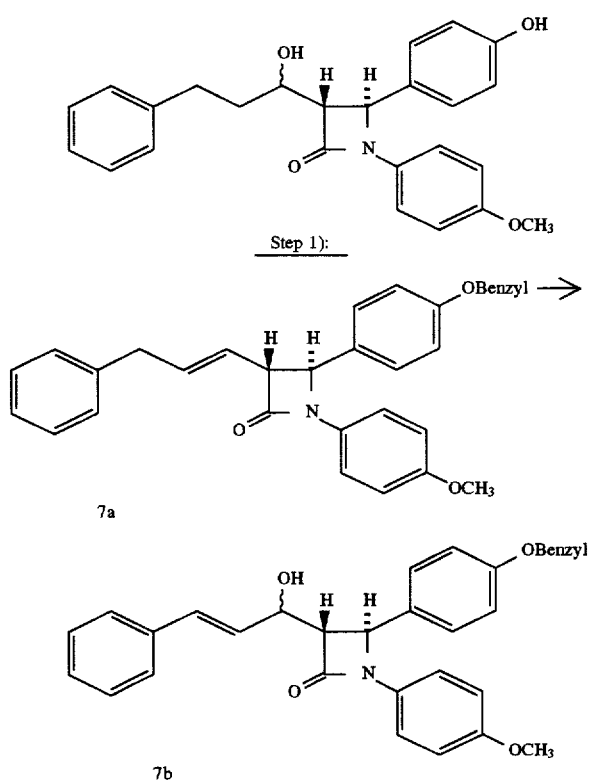

To a solution of 7a (1.0 g, 2.1 mmol) in dioxane (10 ml), add $SeO_2$ (1.33 g, 11.98 mmol) and water (25 ml, 14 mmol), and heat the reaction to 100° C. After 1 h, cool the reaction to room temperature and isolate by extraction the crude product as a diastereomeric mixture (1:2) of alcohols 7b-A and 7b-B. Purify by HPLC on a Dynamax silica column to separate diastereomers 7b-A and 7b-B.

Diastereomer 7b-A (R): oil; $J_{34}=2.3$ Hz, δ C$\underline{H}$(OH)=4.86 (t); HRMS $C_{32}H_{29}NO_4$ calc.: 491.2097; found: 491.2074.

Diastereomer 7b-E (S): oil; $J_{34}=2.3$ Hz, δ C$\underline{H}$(OH)=5.06 (t; HRMS $C_{32}H_{29}NO_4$ calc.: 491.2097; found: 491.2117.

Step 2): To a solution of diastereomer A from step 1 (58 mg, 0.12 mmol) in EtOAc (2 ml), add 10% Pd on carbon (20 mg) and stir at 22° C. under $H_2$ gas (14 psi) for 12 h. Filter and concentrate to obtain the title compound as a semisolid, m.p. 90°–92° C. $J_{34}=2.3$ Hz, δ C$\underline{H}$(OH)=4.1 (m); HRMS $C_{25}H_{25}NO_4$ calc.: 403.1783; found: 403.1792.

EXAMPLE 8

To a solution of the product of Example 4A (90 mg, 0.2 mmol) in $CH_2Cl_2$, add acetyl chloride (80 mg, 1.0 mmol) and pyridine (8 mg, 0.1 mmol) and stir at room temperature for 1 h. Add water, separate the layers and isolate the corresponding acetoxy compound, 8A. In a similar manner, treat the products of Examples 4B, 6B and 6A to obtain the following compounds 8B, 8° C. and 8D, respectively:

8A: 1,4(S)-bis(4-methoxyphenyl)-3(R)-(3(R)-acetoxy-3-phenylpropyl)-2-azetidinone. CI (M⁺H) 460; HRMS $C_{28}H_{29}NO_5$ calc.: 459.2044; found: 459.2045.

8B: 1,4(S)-bis(4-methoxyphenyl)-3(R)-(3(S)-acetoxy-3-phenylpropyl)-2-azetidinone. CI (M⁺H) 460; HRMS $C_{28}H_{29}NO_5$ calc.: 459.2044; found: 459.2048.

8C: 4(S)-(4-acetyloxyphenyl)-3(R)-(3(R)-acetyloxi-3-(4-fluorophenyl)propyl)-1-(4-fluorophenyl)-2-azetidinone. FAB M:S 493.4; HRMS $C_{28}H_{25}F_2NO_5$ calc.: 493.1695; found: 493.1701.

8D: 4(S)-(4-acetyloxyphenyl)-3(R)-(3(S)-acetyloxy-3-(4-fluorophenyl)propyl)-1-(4-fluorophenyl)-2-azetidinone. FAB MS 493.4; HRMS $C_{28}H_{25}F_2NO_5$ calc.: 493.1695; found: 493.1694.

Using appropriate starting materials in the procedure of Example 6, prepare 1-(4-chlorophenyl)-3(R)-(hydroxy-3,(4-chlorophenylpropyl)-4(S)-(4-hydroxyphenyl)-2-azetidinone. Using the procedure of Example 8, prepare the following diacetates 8E and 8F:

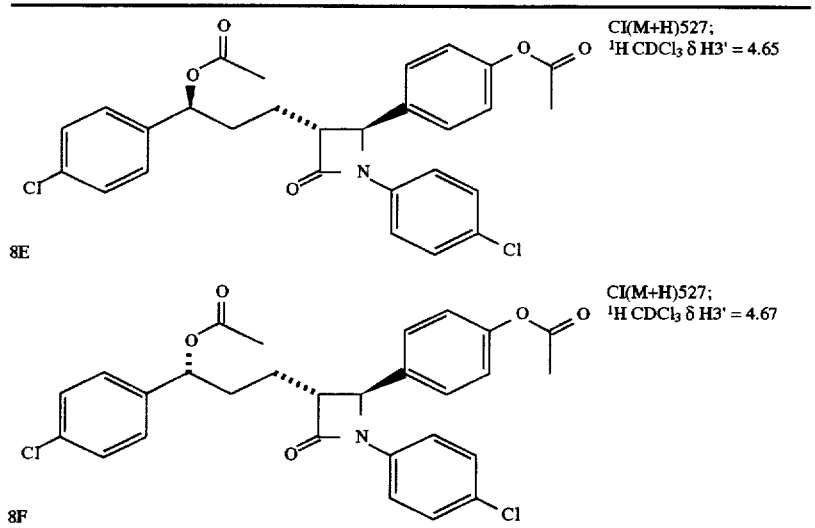

EXAMPLE 9

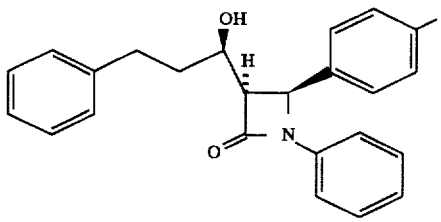

and

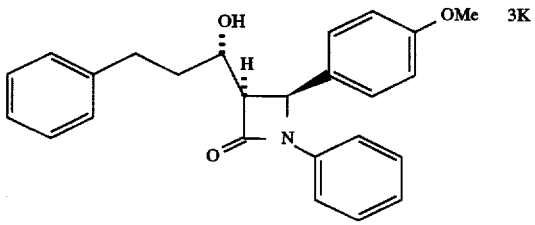

Step 1:

Add pyridinium chlorochromate (2.4 g, 11 mmoles) and $CH_3CO_2Na$ (approx. 20 mg) to a solution of 1-phenyl-3-(3-phenyl-1-hydroxypropyl)-4-(4-methoxyphenyl)-2-azetidinone (2.35 g, 6.1 mmoles) in $CH_2Cl_2$. Stir at room temperature for 18 h, then add silica gel (40 g) and concentrate to dryness. Flash chromatograph the residue using EtOAc:Hex (1:4) to obtain an oil. (1.98 g, yield=85%). $^1H$ NMR 2.85–2.95 (m, 3H), 3.15 (m, 1H), 3.80 (s, 3H), 4.10 (d, 1H, J 2.6), 5.42 (1H, d, 6.85 (dd, 2H, J 2, 8), 7.05 (m, 1 H), 7.2–7.35 (m, 11 H).

Step 2:

To a solution of the product of Step 1 (1.78 g, 4.62 mmoles) in THF at −10° C., add NaH (115 mg ,4.8 mmoles). After 15 min., add NBS (865 mg, 4.85 mmoles) and stir for 20 min., then add 1N HCl and partition between EtOAc and brine. Separate the organic layer, dry ($MgSO_4$) and concentrate to give an oil. Flash chromatograph the oil using EtOAc:Hex (1:10) to collect first 9a as a foamy solid (830 mg, y=39%, FAB MS 466/464, M+H), and then 9b as a colorless solid (1.1 g, y=51%, FAB MS 466/464, M+H).

Step 3a:

Add $Mg(OCOCF_3)_2.CF_3CO_2H$ (7.3 ml of 1M solution in $Et_2O$,) to a solution of 9a (0.68 g, 1.46 mmoles) in THF (5 ml) at −50° C. Stir the reaction 5 min., then add t-Bu—$NH_2$-$BH_3$ (254 mg, 2.92 mmole). After 15 min., allow the reaction to warm to 0° C. over 20 min., add 1N HCl and concentrate in vacuo. Partition the residue between EtOAc and brine. Concentrate the organic layers and dissolve the resultant oil in $CH_2Cl_2$:$CH_3OH$ (1:1) and add ethanolamine (approx 2 mmoles). After 15 min., concentrate the reaction mixture and partition the residue with EtOAc:1N HCl. Wash (brine) and dry ($MgSO_4$) the organic layer to obtain an oil. Purify this oil by flash chromatography using EtOAc:Hex (1:4) to obtain compound 9a-1, a colorless solid, as a 4:1 mix of diastereomers. 0.52 g, y=76%, SIMS 468/466 (M+H).

Step 3b:

Using compound 9b as the starting material, use a procedure similar to Step 3a with $CH_2Cl_2$ as solvent for the preparation of 9b-1 in 80% yield as a 13:1 mixture of diastereomers (SIMS 468/466 M+H).

Step 4a:

Add a solution of 9a-1 (0.27 g, 0.58 mmoles) and AIBN (18 mg, 0.12 mmole) in toluene (40 ml) dropwise over 40 min. to a solution of $(TMS)_3SiH$ (1.0 ml) in toluene at 80° C. After 1 h, add more AIBN (5 mg) 10 and continue at 800° C. for 1.5 h. Cool and concentrate the reaction mixture, dissolve the residue in $CH_3CN$ and wash 3× with hexane. Concentrate the $CH_3CN$ layer to give the title compound as a racemic mixture (0.25 g). Purify this oil by HPLC using a Chiralcel OD column to obtain 3H (major) and 3J (minor).

Step 4b:

Use the procedure of Step 4a, starting with compound 9b-1 to obtain an oil. Purify this by flash chromatography using EtOAc:Hex (1:3) to collect the racemic title compound (y=70%). Purify this oil by HPLC using a Chiralcel OD column to obtain 3J (major) and 3H (minor).

EXAMPLE 10

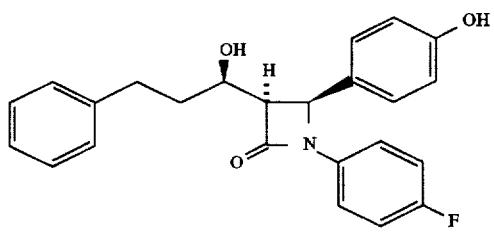

Step 1:

Follow the procedure of Example 3, using 1-(4-fluorophenyl-4-(4-t-butyldimethylsilyloxyphenyl)-2-azetidinone to obtain 1-(4-fluorophenyl-3-(3-phenyl-1-hydroxypropyl) 4-(4-t-butyldimethylsilyl-oxyphenyl)-2-azetidinone.

Step 2:

Treat a solution of the cis-azetidinone of Step 1 (0.25 g) in CH3CN (21 ml) with 48% aqueous HF (2.5 ml). After 18 h, dilute the reaction mixture with cold $H_2O$ and extract with $Et_2O$. Wash (2× $H_2O$, dilute $NaHCO_3$ and brine), dry ($MgSO_4$) and concentrate the $Et_2O$ layer. Crystallize the residue from EtOAc:hexane (1:2) to obtain the title compound as colorless needles (123 mg, y=64%), mp 168°–171° C. Elemental analysis calc for $C_{24}H_{22}O_3FN$: C 73.64; H 5.66; N 3.58. found C 73.32; H 5.65; N 3.68.

The following formulations exemplify some of the dosage of this invention. In each the term "active compound" designates a compound of formula I.

EXAMPLE A

| | Tablets | | |
|---|---|---|---|
| No. | Ingredient | mg/tablet | mg/tablet |
| 1 | Active Compound | 100 | 500 |
| 2 | Lactose USP | 122 | 113 |
| 3 | Corn Starch, Food Grade, as a 10% paste in Purified Water | 30 | 40 |
| 4 | Corn Starch, Food Grade | 45 | 40 |
| 5 | Magnesium Stearate | 3 | 7 |
| | Total | 300 | 700 |

Method of Manufacture

Mix Item Nos. 1 and 2 in suitable mixer for 10–15 minutes. Granulate the mixture with Item No. 3. Mill the damp granules through a coarse screen (e.g., ¼', 0.63 cm) if necessary. Dry the clamp granules. Screen the dried granules if necessary and mix with Item No. 4 and mix for 10–15 minutes. Add Item No. 5 and mix for 1–3 minutes. Compress the mixture to appropriate size and weight on a suitable tablet machine.

EXAMPLE B

| | Capsules | | |
|---|---|---|---|
| No. | Ingredient | mg/tablet | mg/tablet |
| 1 | Active Compound | 100 | 500 |
| 2 | Lactose USP | 106 | 123 |
| 3 | Corn Starch, Food Grade | 40 | 70 |
| 4 | Magnesium Stearate NF | 4 | 7 |
| | Total | 250 | 700 |

Method of Manufacture

Mix Item Nos. 1, 2 and 3 in a suitable blender for 10–15 minutes. Add Item No. 4 and mix for 1–3 minutes. Fill the mixture suitable two-piece hard gelatin capsules on a suitable encapsulating machine.

Representative formulations comprising a cholesterol biosynthesis inhibitor are well known in the art. It is contemplated that where the two active ingredients are administered as a single composition, the dosage forms disclosed above for substituted azetidinone compounds may readily be modified using the knowledge of one skilled in the art.

Using the test procedures described above, the following in vivo data were obtained for the exemplified compounds. Data is reported as percent change (i.e., percent reduction in cholesterol esters) versus control, therefore, negative numbers indicate a positive lipid-lowering effect.

| | % Reduction | | | | % Reduction | | |
|---|---|---|---|---|---|---|---|
| Ex. # | Serum Cholest. | Cholest. Esters | Dose mg/kg | Ex. # | Serum Cholest. | Cholest. Esters | Dose mg/kg |
| 1A | −23 | 0 | 50 | 4C | −12.5 | 0 | 3 |
| 1B | −15 | −39 | 50 | 4D | 9 | 0 | 7 |
| 1C | 14 | 0 | 50 | 4E | 0 | −46 | 3 |
| 2 | 0 | 0 | 50 | 4F | −29 | −95 | 3 |
| 3A | −31 | −69 | 50 | 5 | 0 | −64 | 10 |
| 3C | −60 | −92 | 50 | 6A | −59 | −95 | 1 |
| 3D | −17 | −61 | 10 | 6A-1 | −43 | −93 | 1 |
| 3E | 0 | 0 | 10 | 6B | −40 | −92 | 3 |
| 3F | −29 | −77 | 10 | 6C | 0 | −48 | 3 |
| 3G | −16 | −38 | 10 | 6D | −46 | −95 | 10 |
| 3H | −41 | −86 | 10 | 8A | 0 | −44 | 3 |
| 3I | 0 | −22 | 10 | 8B | −50 | −95 | 3 |
| 3J | 0 | 0 | 3 | 8C | −14 | −37 | 1 |
| 3K | 0 | 0 | 10 | 8D | −49 | −98 | 1 |
| 3L | −15 | −21 | 10 | 8E | −22 | −66 | 3 |
| 3M | 0 | −22 | 10 | 8F | −43 | −94 | 1 |
| 4A | 0 | −54 | 5 | 10 | −26 | −77 | 3 |
| 4B | −37 | −89 | 8 | | | | |

We claim:

1. A compound represented by the formula

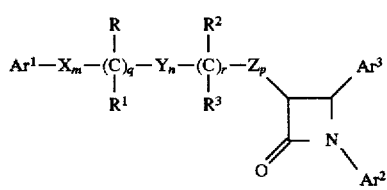

or a pharmaceutically acceptable salt thereof, wherein:

$Ar^1$ and $Ar^2$ are independently selected from the group consisting of aryl and $R^4$-substituted aryl;

$Ar^3$ is aryl or $R^5$-substituted aryl;

X, Y and Z are independently selected from the group consisting of —CH$_2$—, —CH(lower alkyl)- and —C(dilower alkyl)-;

R and R$^2$ are independently selected from the group consisting of —OR$^6$, —O(CO)R$^6$, —O(CO)OR$^9$ and —O(CO)NR$^6$R$^7$;

R$^1$ and R$^3$ are independently selected from the group consisting of hydrogen, lower alkyl and aryl;

q is 0 or 1; r is 0 or 1; m, n and p are independently 0, 1, 2, 3 or 4; provided that at least one of q and r is 1, and the sum of m, n, p, q and r is 2, 3, 4, 5 or 6; and provided that when p is 0 and r is 1, the sum of m, q and n is 1, 2, 3, 4 or 5;

R$^4$ is 1–5 substituents independently selected from consisting of lower alkyl, —OR$^6$, —O(CO)R$^6$, —O(CO)OR$^9$, —O(CH$_2$)$_{1-5}$OR$^6$, —O(CO)NR$^6$R$^7$, —NR$^6$R$^7$, —NR$^6$(CO)R$^7$, —NR$^6$(CO)OR$^9$, —NR$^6$(CO)NR$^7$R$^8$, —NR$^6$SO$_2$R$^9$, —COOR$^6$, —CONR$^6$R$^7$, —COR$^6$, -SO$_2$NR$^6$R$^7$, S(O)$_{0-2}$R$^9$, —O(CH$_2$)$_{1-10}$—COOR$^6$, —O(CH$_2$)$_{1-10}$CONR$^6$R$^7$, -(lower alkylene)COOR$^6$, —CH=CH—COOR$^6$, —CF$_3$, —CN, —NO$_2$ and halogen;

R$^5$ is 1–5 substituents independently selected from the group consisting of —OR$^6$, —O(CO)R$^6$, —O(CO)OR$^9$, —O(CH$_2$)$_{1-5}$OR$^6$, —O(CO)NR$^6$R$^7$, —NR$^6$R$^7$, —NR$^6$(CO)R$^7$, —NR$^6$(CO)OR$^9$, —NR$^6$(CO)NR$^7$R$^8$, —NR$^6$SO$_2$R$^9$, —COOR$^6$, —CONR$^6$R$^7$, —COR$^6$, —SO$_2$NR$^6$R$^7$, S(O)$_{0-2}$R$^9$, —O(CH$_2$)$_{1-10}$—COOR$^6$, —O(CH$_2$)$_{1-10}$CONR$^6$R$^7$, -(lower alkylene)COOR$^6$ and —CH=CH—COOR$^6$;

R$^6$, R$^7$ and R$^8$ are independently selected from the group consisting of hydrogen, lower alkyl, aryl and aryl-substituted lower alkyl; and R$^9$ is lower alkyl, aryl or aryl-substituted lower alkyl.

2. A compound of claim 1 wherein Ar$^1$ is phenyl or R$^4$-substituted phenyl, Ar$^2$ is phenyl or R$^4$-substituted phenyl and Ar$^3$ is R$^5$-substituted phenyl.

3. A compound of claim 2 wherein Ar$^1$ is R$^4$-substituted phenyl wherein R$^4$ is halogen; Ar$^2$ is R$^4$-substituted phenyl wherein R$^4$ is halogen or —OR$^6$, wherein R$^6$ is lower alkyl or hydrogen; and Ar$^3$ R$^5$-substituted phenyl, wherein R$^5$ is —OR$^6$, wherein R6 is lower alkyl or hydrogen.

4. A compound of claim 1 wherein X, Y, and Z are each —CH$_2$—; R$^1$ and R$^3$ are each hydrogen; R and R$^2$ are each —OR$^6$, wherein R$^6$ is hydrogen; and the sum of m, n, p, q and r is 2, 3 or 4.

5. A compound of claim 1 wherein m, n and r are each zero, q is 1 and p is 2.

6. A compound of claim 1 wherein p, q and n are each zero, r is 1 and m is 2 or 3.

7. A compound selected from the group consisting of rel 3(R)-(2(R)-hydroxy-2-phenylethyl)-4(R)-(4-methoxyphenyl)-1-phenyl-2-azetidinone;

rel 3(R)-(2(R)-hydroxy-2-phenylethyl)-4(S)-(4-methoxyphenyl)-1-phenyl-2-azetidinone;

3(S)-(1(S)-hydroxy-3-phenylpropyl)-4(S)-(4-methoxyphenyl)-1-phenyl-2-azetidinone;

3(S)-(1(R)-hydroxy-3-phenylpropyl)-4(S)-(4-methoxyphenyl)-1-phenyl-2-azetidinone;

3(R)-(1(R)-hydroxy-3-phenylpropyl)-4(S)-(4-methoxyphenyl)-1-phenyl-2-azetidinone;

rel-3(R)-[(S)-hydroxy-(2-naphthalenyl)methyl]-4(3S)-(4-methoxyphenyl)-1-phenyl)-1 -phenyl-2-azetidinone;

rel-3(R)-[(R)-hydroxy-(2-naphthalenyl)methyl]-4(S)-(4-methoxyphenyl)-1-phenyl-2-azetidinone;

3(R)-(3(R)-hydroxy-3-phenylpropyl)-1,4(S)-bis-(4-methoxyphenyl)-2-azetidinone;

3(R)-(3(S)-hydroxy-3-phenylpropyl)-1,4(S)-bis-(4-methoxyphenyl)-2-azetidinone;

4(S)-(4-hydroxyphenyl)-3(R)-(3(R)-hydroxy-3-phenylpropyl-1-(4-methoxyphenyl)-2-azetidinone;

4(S)-(4-hydroxyphenyl)-3(R)-(3(S)-hydroxy-3-phenylpropyl-1-(4-methoxyphenyl)-2-azetidinone;

rel 3(R)-[3(RS)-hydroxy-3-[4-(methoxymethoxy)-phenyl]-1,4(S)-bis-(4-methoxyphenyl)-2-azetidinone;

1-(4-fluorophenyl)-3(R)-[3(S)-(4-fluorophenyl)-3-hydroxypropyl)]-4(S)-($^4$-hydroxyphenyl)-2-azetidinone;

1-(4-fluorophenyl)-3(R)-[3(R)-(4-fluorophenyl)-3-hydroxypropyl)]-4(S)-(4-hydroxyphenyl)-2-azetidinone;

4(S)-[4-(acetyloxy)phenyl]-3(R)-(3(R)-hydroxy-3-phenylpropyl)-1-(4-methoxyphenyl)-2-azetidinone;

4(S)-[4-(acetyloxy)phenyl]-3(R)-(3(S)-hydroxy-3-phenylpropyl)-1(4-methoxyphenyl)-2-azetidinone;

1-($^4$-fluorophenyl)-3(R)-[3(S)-(4-fluorophenyl)-3-hydroxypropyl)]-4(S)-[4-(phenylmethoxy)phenyl]-2-azetidinone;

3(R)-[3(R)-acetyloxy)-3-phenylpropyl]-1,4(S)-bis-(4-methoxyphenyl)-2-azetidinone;

3(R)-[3(S)-acetyloxy)-3-phenylpropyl]-1,4(S)-bis-(4-methoxyphenyl)-2-azetidinone;

3(R)-[3(R)-(acetyloxy)-3-(4-fluorophenyl)propyl]-4(S)-[4-(acetyloxy)phenyl]-1-(4-fluorophenyl)-2-azetidinone;

3(R)-[3(S)-(acetyloxy)-3-(4-fluorophenyl)propyl]-4(S)-[4-(acetyloxy)phenyl]-1-(4-fluorophenyl)-2-azetidinone;

3(R)-[3(R)-(acetyloxy)-3-(4-chlorophenyl)propyl]-4(S)-[4-(acetyloxy)phenyl]-1-(4-chlorophenyl)-2-azetidinone;

3(R)-[3(S)-(acetyloxy)-3-(4-chlorophenyl)propyl]-4(S)-[4-(acetyloxy)phenyl]-1-(4-chlorophenyl)-2-azetidinone; and rel 1-(4-fluorophenyl)-4(S)-(4-hydroxyphenyl)-3(1R)-(1(R)-hydroxy-3-phenylpropyl)-2-azetidinone.

8. A pharmaceutical composition for the treatment prevention of atherosclerosis, or for the reduction of plasma cholesterol levels, comprising an effective amount of a compound of claim 1 in a pharmaceutically acceptable carrier.

9. A method of treating or preventing atherosclerosis or reducing plasma cholesterol levels comprising administering to a mammal in need of such treatment an effective amount of a compound of claim 1.

* * * * *

UNITED STATES PATENT AND TRADEMARK OFFICE
CERTIFICATE OF CORRECTION

PATENT NO. : 5,767,115
DATED : JUNE 16, 1998
INVENTOR(S) : STUART B. ROSENBLUM, SUNDEEP DUGAR, DUANE A. BURNETT, JOHN W. CLADER AND BRIAN A. MCKITTRICK

It is certified that error appears in the above-identified patent and that said Letters Patent is hereby corrected as shown below:

In column 40, line 3, change "4(3S)" to read --4(S)--.

In column 40, line 17, change "phenyl]-1,4(S)' " to read --phenyl]propyl]-1,4(S)--.

In column 40, line 19, change "(4-hydroxyphenyl)" to read --(4-hydroxyphenyl)--.

In column 40, line 29, change "(4-fluorophenyl)" to read --(4-fluorophenyl)--.

Signed and Sealed this

Fifteenth Day of September, 1998

Attest:

BRUCE LEHMAN

*Attesting Officer*    *Commissioner of Patents and Trademarks*